US006581011B1

(12) United States Patent
Johnson et al.

(10) Patent No.: US 6,581,011 B1
(45) Date of Patent: *Jun. 17, 2003

(54) ONLINE DATABASE THAT INCLUDES INDICES REPRESENTATIVE OF A TISSUE POPULATION

(75) Inventors: Peter C. Johnson, Wexford, PA (US); Mary Del Brady, Pittsburgh, PA (US)

(73) Assignee: TissueInformatics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/338,908

(22) Filed: Jun. 23, 1999

(51) Int. Cl.[7] .............................. G01N 3/00; G06K 9/00; G06F 7/00; G06F 12/00; G06F 17/00
(52) U.S. Cl. .............................. 702/19; 435/6; 435/7.1; 382/128; 382/133; 707/102; 707/200; 73/788; 73/826
(58) Field of Search .............................. 435/6; 128/664; 702/19; 364/300

(56) References Cited

U.S. PATENT DOCUMENTS

| | | | |
|---|---|---|---|
| 5,506,098 A | * | 4/1996 | Zarling et al. .................. 435/6 |
| 5,526,258 A | | 6/1996 | Bacus |
| 5,640,453 A | * | 6/1997 | Schuchman et al. .......... 380/10 |
| 5,668,634 A | * | 9/1997 | Newman ...................... 356/445 |
| 5,713,364 A | * | 2/1998 | DeBaryshe et al. .......... 128/664 |
| 5,785,663 A | * | 7/1998 | Sarvazyan ................... 600/587 |
| 5,836,872 A | * | 11/1998 | Kenet et al. ................. 600/306 |
| 5,836,877 A | * | 11/1998 | Zavislan ...................... 600/407 |
| 5,891,619 A | | 4/1999 | Zakim |
| 5,901,237 A | * | 5/1999 | Conrad ........................ 382/110 |
| 5,933,519 A | | 8/1999 | Lee |
| 6,026,174 A | | 2/2000 | Palcic et al. |
| 6,104,835 A | | 8/2000 | Han |
| 6,136,955 A | * | 10/2000 | Hillman et al. .............. 530/350 |
| 6,238,342 B1 | | 5/2001 | Feleppa et al. |
| 6,246,785 B1 | | 6/2001 | Molnar et al. |

OTHER PUBLICATIONS

B Johannes et al., MEDINFO 95 Proceedings, "Differentiation of Normal and Pathologic Brain Structures in MRI Using Exact T1 and T2 Values Followed by a Multidimensional Cluster Analysis," 1995, pp. 687–691.*

Jamin et al. "Highly resolved chemical imaging of living cells by using synchrotron infrared microscopy" Proc. Natl. Acad. Sci. USA, vol. 95, pp. 4837–4840, 1998.*

Persoon–Rothert et al. "Oxidative stress–induced perturbations of calcium homeostasis and cell death in cultured myocytes: role of extracellular calcium" Molecular and Cellular Biochemistry vol. 136 pp. 1–9, 1994.*

Ellenberg et al. "Two–color green fluorescent protein time-–lapse imaging" Biotechniques vol. 25, pp. 838–846, 1998.*

Warren et al. "Combing Ultrasound and Fluorescence Spectroscopy for Physico–Chemical Imaging of Athersclerosis" IEEE Transactions on Biomedical Engineering vol. 42 pp. 121–132, 1995.*

Xing et al. "Preservation of Specific RNA Distribution within the Chromatin–dpleted Nuclear Substructure Demonstrated by in Situ Hybridization Coupled with Biochemical Fractionation" The Journal of Cellular Biology vol. 112, pp. 1055–1063, 1991.*

Lawrence et al. "Quantitative analysis of the in situ hybridization methods for the detection of actin gene expression" Nucleic Acids Research vol. 13, pp. 1777–1799, 1985.*

* cited by examiner

*Primary Examiner*—Marianne P. Allen
(74) *Attorney, Agent, or Firm*—Nanda P.B.A. Kumar; Louis M. Heidelberger; Lawrence B. Ebert

(57) ABSTRACT

A sample of normal tissue specimens obtained from a subset of a population of subjects with shared characteristics is profiled in order to generate a plurality of structural indices that correspond to statistically significant representations of characteristics of tissue associated with the population. The structural indices include cell density, matrix density, blood vessel density and layer thickness. Alternatively, the sample of normal tissue specimens obtained from the subset of the population of subjects with shared characteristics can also be profiled in order to generate a plurality of cell function and/or mechanical indices that correspond to statistically significant representations of characteristics of tissue associated with the population. Structural, mechanical and/or cell function indices for a plurality of tissue populations are determined and then stored in a database, and subscribers/users are granted access to all or part of the database based on a subscription fee. In addition to using the information in the database for general research purposes, subscribers may use the database information to classify tissue specimens (e.g., human tissue specimens, animal tissue specimens, plant tissue specimens, food tissue specimens, or manufactured tissue specimens) provided by the subscriber. In particular, a subscriber can measure parameters (e.g., structural, mechanical and/or cell function indices) associated with the subscriber's tissue specimens and then compare this information to corresponding parameters for normal tissue in the database in order to classify the subscriber's tissue specimens as either normal or abnormal.

87 Claims, 17 Drawing Sheets

| TISSUE POPULATION | TISSUE TYPE | RACE OF POPULATION | GENDER POPULATION | AGE BRACKET OF POPULATION | GEOGRAPHIC LOCATION OF POPULATION |
|---|---|---|---|---|---|
| TISSUE LAYER NO. | | | | | |
| AVERAGE LAYER THICKNESS | | | | | |
| INDEX OF DISPERSION ABOUT AVERAGE THICKNESS | | | | | |
| AVERAGE CELL DENSITY INDEX (CELL TYPE 1) | | | | | |
| INDEX OF DISPERSION ABOUT AVERAGE CELL DENSITY (CELL TYPE 1) | | | | | |
| AVERAGE CELL DENSITY INDEX (CELL TYPE 2) | | | | | |
| INDEX OF DISPERSION ABOUT AVERAGE CELL DENSITY (CELL TYPE 2) | | | | | |
| ⋮ | | | | | |
| AVERAGE CELL DENSITY INDEX (CELL TYPE m) | | | | | |
| INDEX OF DISPERSION ABOUT AVERAGE CELL DENSITY (CELL TYPE m) | | | | | |
| AVERAGE MATRIX DENSITY INDEX | | | | | |
| INDEX OF DISPERSION ABOUT AVERAGE MATRIX DENSITY (MATRIX TYPE 1) | | | | | |
| AVERAGE RELATIVE CELL LOCATION INDEX (CELL TYPE 1 / CELL TYPE 2) | | | | | |
| INDEX OF DISPERSION ABOUT AVERAGE REL. LOC. INDEX (CELL TYPE 1 / CELL TYPE 2) | | | | | |
| AVERAGE RELATIVE CELL LOCATION INDEX (CELL TYPE 1 / CELL TYPE 3) | | | | | |
| INDEX OF DISPERSION ABOUT AVERAGE REL. LOC. INDEX (CELL TYPE 1 / CELL TYPE 3) | | | | | |
| ⋮ | | | | | |
| AVERAGE RELATIVE CELL LOCATION INDEX (CELL TYPE x / CELL TYPE y) | | | | | |
| INDEX OF DISPERSION ABOUT AVERAGE REL. LOC. INDEX (CELL TYPE x / CELL TYPE y) | | | | | |
| AVERAGE RELATIVE BLOOD VESSEL LOC. INDEX (CELL TYPE 1 / BLOOD VESSELS) | | | | | |
| INDEX OF DISPERSION ABOUT AVERAGE REL. LOC. INDEX (CELL TYPE 1 / BLOOD VESSELS) | | | | | |
| AVERAGE RELATIVE BLOOD VESSEL LOC. INDEX (CELL TYPE 2 / BLOOD VESSELS) | | | | | |
| INDEX OF DISPERSION ABOUT AVERAGE REL. LOC. INDEX (CELL TYPE 2 / BLOOD VESSELS) | | | | | |
| ⋮ | | | | | |
| AVERAGE RELATIVE BLOOD VESSEL LOC. INDEX (CELL TYPE n / BLOOD VESSELS) | | | | | |
| INDEX OF DISPERSION ABOUT AVERAGE REL. LOC. INDEX (CELL TYPE n / BLOOD VESSELS) | | | | | |

FIG. 5

| TISSUE POPULATION | TISSUE TYPE | RACE OF POPULATION | GENDER POPULATION | AGE BRACKET OF POPULATION | GEOGRAPHIC LOCATION OF POPULATION |
|---|---|---|---|---|---|
| TISSUE LAYER NO. ||||||
| AVERAGE ELASTICITY INDEX ||||||
| INDEX OF DISPERSION ABOUT AVERAGE ELASTICITY ||||||
| AVERAGE BREAKING STRENGTH INDEX ||||||
| INDEX OF DISPERSION ABOUT AVERAGE BREAKING STRENGTH ||||||

FIG. 6

| TISSUE POPULATION | | TISSUE LAYER NO. |
|---|---|---|
| DNA (TYPE 1) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| DNA (TYPE 2) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| ⋮ | ⋮ | |
| DNA (TYPE m) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| mRNA (TYPE 1) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| mRNA (TYPE 2) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| ⋮ | ⋮ | |
| mRNA (TYPE m) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |

FROM FIG. 7A

| TISSUE POPULATION | | TISSUE LAYER NO. |
|---|---|---|
| CELLULAR PROTEIN (TYPE 1) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| CELLULAR PROTEIN (TYPE 2) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| ⋮ | ⋮ | |
| CELLULAR PROTEIN (TYPE m) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| CELLULAR LIPID (TYPE 1) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| CELLULAR LIPID (TYPE 2) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |
| ⋮ | ⋮ | |
| CELLULAR LIPID (TYPE m) | AVERAGE AMOUNT INDEX | |
| | INDEX OF DISPERSION ABOUT AVERAGE AMOUNT | |
| | AVERAGE LOCATION INDEX | |
| | INDEX OF DISPERSION ABOUT AVERAGE LOCATION | |

FROM FIG. 7B

| | |
|---|---|
| DNA (TYPE 1) | AVERAGE AMOUNT INDEX |
| | INDEX OF DISPERSION ABOUT AVERAGE AMOUNT |
| | AVERAGE LOCATION INDEX |
| | INDEX OF DISPERSION ABOUT AVERAGE LOCATION |
| DNA (TYPE 2) | AVERAGE AMOUNT INDEX |
| | INDEX OF DISPERSION ABOUT AVERAGE AMOUNT |
| | AVERAGE LOCATION INDEX |
| | INDEX OF DISPERSION ABOUT AVERAGE LOCATION |
| ⋮ | ⋮ |
| DNA (TYPE m) | AVERAGE AMOUNT INDEX |
| | INDEX OF DISPERSION ABOUT AVERAGE AMOUNT |
| | AVERAGE LOCATION INDEX |
| | INDEX OF DISPERSION ABOUT AVERAGE LOCATION |

FIG. 7C

| TISSUE POP. | INDICES | | |
|---|---|---|---|
| LUNG | STRUCTURAL INDICES (FIG. 5) | MECHANICAL INDICES (FIG. 6) | CELL FUNCTION INDICES (FIGS. 7A, 7B, 7C) |
| INTESTINE | STRUCTURAL INDICES (FIG. 5) | MECHANICAL INDICES (FIG. 6) | CELL FUNCTION INDICES (FIGS. 7A, 7B, 7C) |
| CARTILAGE | STRUCTURAL INDICES (FIG. 5) | MECHANICAL INDICES (FIG. 6) | CELL FUNCTION INDICES (FIGS. 7A, 7B, 7C) |
| EYE | STRUCTURAL INDICES (FIG. 5) | MECHANICAL INDICES (FIG. 6) | CELL FUNCTION INDICES (FIGS. 7A, 7B, 7C) |
| BONE | STRUCTURAL INDICES (FIG. 5) | MECHANICAL INDICES (FIG. 6) | CELL FUNCTION INDICES (FIGS. 7A, 7B, 7C) |
| FAT | STRUCTURAL INDICES (FIG. 5) | MECHANICAL INDICES (FIG. 6) | CELL FUNCTION INDICES (FIGS. 7A, 7B, 7C) |
| MUSCLE | STRUCTURAL INDICES (FIG. 5) | MECHANICAL INDICES (FIG. 6) | CELL FUNCTION INDICES (FIGS. 7A, 7B, 7C) |
| KINDEY | STRUCTURAL INDICES (FIG. 5) | MECHANICAL INDICES (FIG. 6) | CELL FUNCTION INDICES (FIGS. 7A, 7B, 7C) |
| BRAIN | STRUCTURAL INDICES (FIG. 5) | MECHANICAL INDICES (FIG. 6) | CELL FUNCTION INDICES (FIGS. 7A, 7B, 7C) |
| HEART | STRUCTURAL INDICES (FIG. 5) | MECHANICAL INDICES (FIG. 6) | CELL FUNCTION INDICES (FIGS. 7A, 7B, 7C) |
| LIVER | STRUCTURAL INDICES (FIG. 5) | MECHANICAL INDICES (FIG. 6) | CELL FUNCTION INDICES (FIGS. 7A, 7B, 7C) |
| SKIN | STRUCTURAL INDICES (FIG. 5) | MECHANICAL INDICES (FIG. 6) | CELL FUNCTION INDICES (FIGS. 7A, 7B, 7C) |

FIG. 8

ONLINE DATABASE THAT INCLUDES INDICES REPRESENTATIVE OF A TISSUE POPULATION

BACKGROUND OF THE INVENTION

I. Field of the Invention

The present invention relates to methods for profiling, engineering, manufacturing and classifying various types of tissue. More particularly, the present invention relates to the development and use of a novel tissue information database for engineering, manufacturing and classifying various types of tissue. The novel database includes structural, cell function and/or mechanical indices that correspond to statistically significant representations of tissue characteristics associated with various tissue populations.

II. Description of the Related Art

Currently a clear understanding exists of the gross anatomy of the human body (i.e., structural information at the macroscopic level.) Sequencing of human genome has provided information at the genetic level (molecular and submicroscopic.) However, little if any reliable structural information exists at the tissue level (1–1000 microns, i.e., microscopic to mesoscopic.) It is believed that if reliable, multi-dimensional tissue structural information existed, such information would serve to enhance and accelerate new advances in tissue engineering, drug design, gene discovery and genomics research.

Tissue engineering is an emerging segment within the biotechnology industry. Currently, an approach known as "random" tissue engineering is used for making simple two-dimensional tissues that do not require a blood supply, e.g., skin and cartilage. In the random tissue engineering approach, cells are placed in suspension on culture plates or within sponge-like polymer matrices and the respective tissues are grown in incubators with minimal intervention. While structurally simple tissues may be manufactured today in this manner, there is general agreement that this approach will not work for more complex tissues such as muscle and vascularized organs, and that these applications will require more complex growth environments whose applications will depend on tissue knowledge. Rather than using random tissue engineering. Applicants believe that a new methodology referred to as "rational" tissue engineering will be required to make more complex tissues such as muscle and vascularized organs. Applicants believe that rational tissue engineering will use structural information at the tissue level, as well as mechanical and cell function information on tissue, in order to develop complex three-dimensional "blueprints" of tissue. These blueprints will then be used to manufacture complex tissue on a microscopic level by delivering the proper cells and intercellular constituents required for generation of the tissue during the manufacturing process.

In order for the rational tissue engineering approach discussed above to be successful, structural information at the tissue level, as well as mechanical and cell function information on tissue, will be required and such information must be made accessible to persons in the tissue engineering, drug design and genomics research fields. It is an object of the present invention to develop such tissue information and to provide this information to persons and entities in the tissue engineering/manufacturing, drug design and genomics research fields. It is a further object of the present invention to use this tissue information to evaluate, classify and/or perform quality control on living and manufactured tissue specimens provided by tissue suppliers. With respect to manufactured tissue specimens, it is a particular object of the present invention to use the tissue information that is the subject of the present invention to identify normal elements of such manufactured tissue specimens in cases where, for example, such manufactured tissue specimens do not appear normal in total but contain elements that appear and/or function normally.

These and other objects will become apparent from the description which follows.

SUMMARY OF THE INVENTION

The present invention is directed to an online database that includes indices representative of a tissue population. In the method of the present invention, a sample of normal tissue specimens obtained from a subset of a population of subjects with shared characteristics are profiled in order to generate a plurality of structural indices that correspond to statistically significant representations of characteristics of tissue associated with the population. The structural indices include cell density, matrix density, blood vessel density and layer thickness.

In one embodiment, the tissue specimens obtained from the subset of the population are profiled by imaging a plurality of sections of each tissue specimen from the subset. Distributions of cell density values, matrix density values and blood vessel density values associated with the plurality of sections are then determined in accordance with the results of the imaging. A cell density index representative of tissue associated with the population is determined in accordance with the distribution of cell density values, a matrix density index representative of tissue associated with the population is determined in accordance with the distribution of matrix density values, and a blood vessel density index representative of tissue associated with the population is determined in accordance with the distribution of blood vessel density values. In one example, the cell density index is determined by calculating a statistical average of the distribution of cell density values, the matrix density index is determined by calculating a statistical average of the distribution of matrix density values, and the blood vessel density index is determined by calculating a statistical average of the distribution of blood vessel density values. Each statistical average of a distribution values represents, for example, a mean, median or mode of the distribution of values.

In accordance with a further aspect, the structural indices include a further cell density index corresponding to an index of dispersion of the distribution of cell density values, a further matrix density index corresponding to an index of dispersion of the distribution of matrix density values, and a further blood vessel density index corresponding to an index of dispersion of the distribution of blood vessel density values. Each index of dispersion of a distribution values represents, for example, a standard deviation, standard error of the mean or range of the distribution of values.

In accordance with a still further aspect, distributions of relative cell location values, relative matrix location values and relative blood vessel location values associated with the plurality of sections are also determined in accordance with the results of the imaging. A relative cell location index representative of tissue associated with the population is determined in accordance with the distribution of relative cell location values, a relative matrix location index representative of tissue associated with the population is determined in accordance with the distribution of relative matrix location values, and a relative blood vessel location index representative of tissue associated with the population is determined in accordance with the distribution of relative blood vessel location values. In one example, the relative cell location index is determined by calculating a statistical average of the distribution of relative cell location values, the relative matrix location index is determined by calculating a statistical average of the distribution of relative matrix location values, and the relative blood vessel location index is determined by calculating a statistical average of the distribution of relative blood vessel location values.

In accordance with yet a further aspect, the structural indices include a further relative cell location index corresponding to an index of dispersion of the distribution of relative cell location values, a further relative matrix location index corresponding to an index of dispersion of the distribution of relative matrix location values, and a further relative blood vessel location index corresponding to an index of dispersion of the distribution of relative blood vessel location values. Again, each index of dispersion of a distribution values represents, for example, a standard deviation, standard error of the mean or range of the distribution of values.

Various imaging modalities may be used for profiling the tissue specimens and generating the structural indices described above. For example, light microscopy, fluorescent microscopy, spectral microscopy, hyper-spectral microscopy, electron microscopy, confocal microscopy and optical coherence tomography may be used for profiling the tissue specimens in accordance with the present invention. A combination of such imaging modalities can also be used for profiling tissue specimens in accordance with the present invention.

In addition to structural indices described above, one or more mechanical indices may be determined from the normal tissue specimens. In accordance with this aspect of the invention, the sample of normal tissue specimens obtained from the subset of the population with shared characteristics is further profiled in order to generate one or more mechanical indices that correspond to statistically significant representations of characteristics of tissue associated with the population. One of the mechanical indices may correspond to a modulus of elasticity associated with the normal tissue specimens. The mechanical index corresponding to the modulus of elasticity is preferably determined by obtaining a distribution of elasticity values associated with the plurality of sections discussed above, and then determining an elasticity index representative of tissue associated with the population in accordance with the distribution of elasticity values. The elasticity index preferably represents the statistical average (e.g., mean, median or mode) of the distribution of elasticity values. In accordance with a further aspect, a further elasticity index representative of the index of dispersion of the distribution of elasticity values is determined. This further elasticity index preferably represents the standard deviation, standard error of the mean or range of the distribution of elasticity values.

A further mechanical index corresponding to the mechanical strength (e.g., breaking or tensile strength) associated with the normal tissue specimens may also be determined. The mechanical index corresponding to the breaking strength is preferably determined by obtaining a distribution of breaking strength values associated with the plurality of sections discussed above, and then determining a breaking strength index representative of tissue associated with the population in accordance with the distribution of breaking strength values. The breaking strength index preferably represents the statistical average (e.g., mean, median or mode) of the distribution of breaking strength values. In accordance with a further aspect, a further breaking strength index representative of the index of dispersion of the distribution of breaking strength values is determined. This further breaking strength index preferably represents the standard deviation, standard error of the mean or range of the distribution of breaking strength values.

In addition to structural and mechanical indices, one or more cell function indices may be determined from the normal tissue specimens. In accordance with this aspect of the invention, a plurality of cell function assays are performed on the sample of normal tissue specimens from the subset of the population of subjects with shared characteristics. The results of the cell function assays are used to generate a plurality of cell function indices that correspond to statistically significant representations of characteristics of tissue associated with the population. The cell function indices are optionally used to form a cell function map that is stored in a tissue information database. In an alternate embodiment, only the cell function indices and/or the cell function map (and not the structural or mechanical indices) are determined. The cell function indices used in connection with this aspect of the invention correspond, for example, to (i) location, type and amount of DNA in the normal tissue specimens from the subset, (ii) location, type and amount of mRNA in the normal tissue specimens from the subset, (iii) location, type and amount of cellular proteins in the normal tissue specimens from the subset, (iv) location, type and amount of cellular lipids in the normal tissue specimens from the subset, and/or (v) location, type and amount of cellular ion distributions in the normal tissue specimens from the subset.

In accordance with further aspects of the invention, the correlation between various one of the indices described above may also be determined. For example, a correlation between two structural indices, a correlation between two mechanical indices, a correlation between two cell function indices, a correlation between a structural index and a mechanical index, a correlation between a structural index and a cell function index, and/or a correlation between a mechanical index and a cell function index may also be determined.

The normal tissue specimens profiled to generate the structural, mechanical and/or cell function indices described above correspond, for example, to a set of either normal intestine tissue specimens, normal cartilage tissue specimens, normal eye tissue specimens, normal bone tissue specimens, normal fat tissue specimens, normal muscle tissue specimens, normal kidney tissue specimens, normal brain tissue specimens, normal heart tissue specimens, normal liver tissue specimens, normal skin tissue specimens, normal pleura tissue specimens, normal peritoneum tissue specimens, normal pericardium tissue specimens, normal dura-mater tissue specimens, normal oral-nasal mucus membrane tissue specimens, normal pancreas tissue specimens, normal spleen tissue specimens, normal gall bladder tissue specimens, normal blood vessel tissue specimens, normal bladder tissue specimens, normal uterus tissue specimens, normal ovarian tissue specimens, normal urethra tissue specimens, normal penile tissue specimens, normal vaginal tissue specimens, normal esophagus tissue specimens, normal anus tissue specimens, normal adrenal gland tissue specimens, normal ligament tissue specimens, normal intervertebral disk tissue specimens, normal bursa tissue specimens, normal meniscus tissue specimens, normal fascia tissue specimens, normal bone marrow tissue specimens, normal tendon tissue specimens, normal pulley tissue specimens, normal tendon sheath tissue specimens, normal lymph node tissue specimens, or normal nerve tissue specimens. In further embodiments, the tissue specimens profiled correspond to plant or animal tissue types, composite tissue types, virtual tissue types or food tissue types.

In accordance with a further aspect, the present invention is directed to a computer implemented method for providing information representative of a plurality of tissue types to a subscriber. Tissue information representative of a plurality of tissue types (e.g., the structural, mechanical and/or cell function indices described above for a plurality of tissue types and the correlation results described above for a plurality of tissue types) is stored in a database. For each tissue type, the database includes, for example, a plurality of structural indices generated from a sample of normal tissue specimens obtained from a subset of a population of subjects with shared characteristics. The structural indices correspond to statistically significant representations of characteristics of tissue associated with the population. The plurality of structural indices include cell density, matrix density, blood vessel density and layer thickness. For each tissue type, the database alternatively includes a plurality of the cell function and/or mechanical indices described above either alone, or in combination with the aforementioned structural indices. Subscribers or users interested in engineering, classifying, manufacturing or analyzing tissue are provided access to the database in exchange for a subscription fee. The subscribers may optionally measure parameters associated with subscriber-supplied tissue samples. The subscriber-supplied tissue samples are then classified by comparing measured parameters associated with the subscriber-supplied tissue samples with the tissue information stored in the database (e.g., the structural, mechanical and/or cell function indices described above and/or the correlation results described above.) In addition to the other tissue types described above, the database optionally stores indices representative of one or more abnormal tissue types, and the subscriber-supplied tissue samples are classified as either normal or abnormal by comparing measured parameters associated with the subscriber-supplied tissue samples to the tissue information stored in the database. Where the subscriber-supplied tissue specimens correspond to manufactured tissue specimens, measured parameters associated with the subscriber-supplied tissue samples may be compared to the tissue information stored in the database in order to identify normal elements of such manufactured tissue specimens in cases where, for example, such manufactured tissue specimens do not appear normal in total but contain elements that appear and/or function normally.

BRIEF DESCRIPTION OF THE DRAWINGS

The features, objects, and advantages of the present invention will become more apparent from the detailed description set forth below when taken in conjunction with the drawings.

FIG. 5 is a diagram of an exemplary data structure for storing structural indices associated with a given tissue type (or population of tissue specimens) in a database.

FIG. 6 is a diagram of an exemplary data structure for storing mechanical indices associated with a given tissue type (or population of tissue specimens) in a database.

FIGS. 7A–7C are a diagram of an exemplary data structure for storing cell function indices associated with a given tissue type (or population of tissue specimens) in a database.

FIG. 8 is a diagram of a database for storing structural, mechanical and cell function indices associated with a plurality of different tissue types.

DETAILED DESCRIPTION OF THE INVENTION

Figure 1:
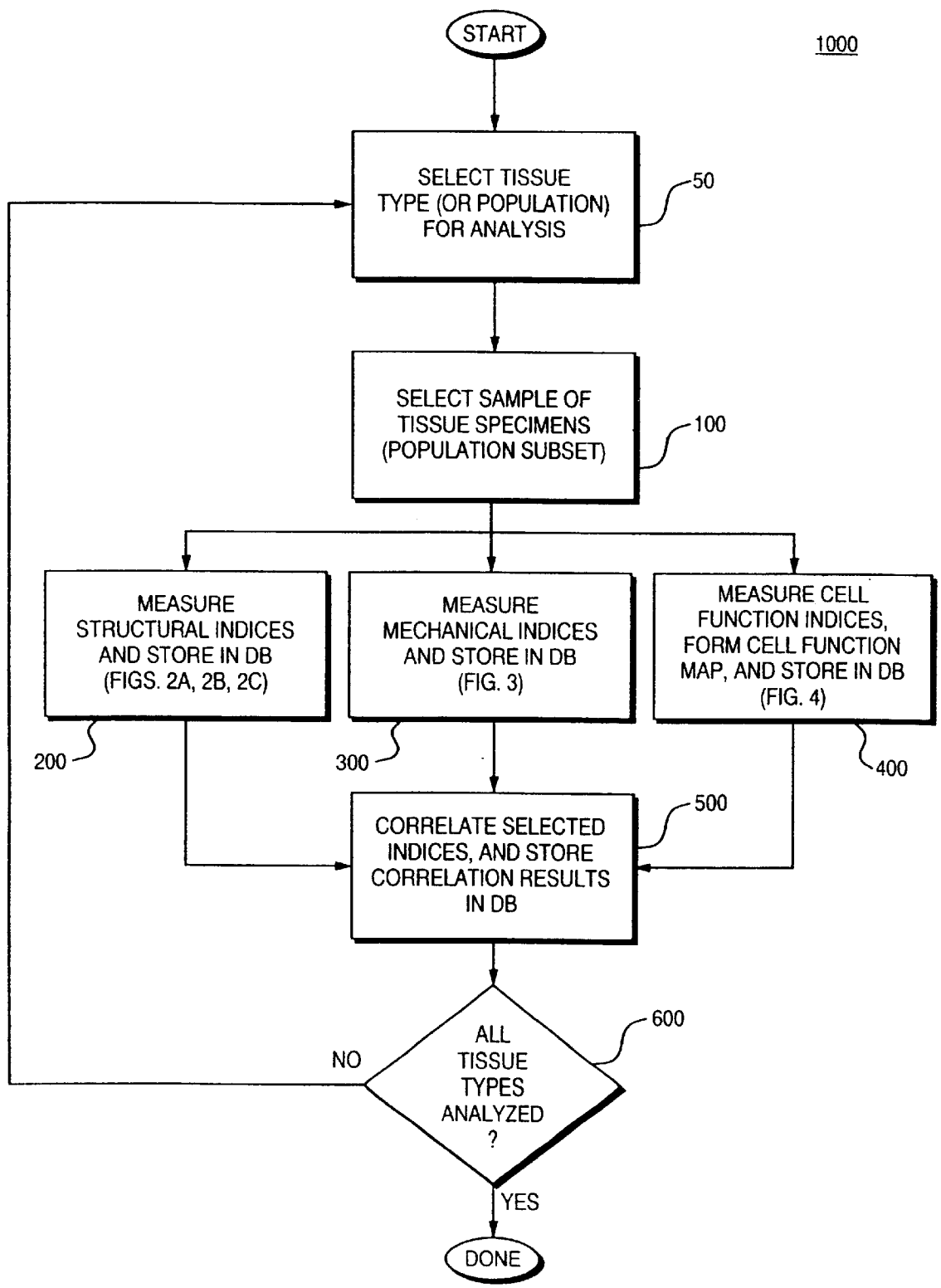
FIG. 1 is a flow diagram of a method for profiling samples of normal tissue specimens. In the method shown, each sample profiled is obtained from a subset of a population of subjects with shared characteristics, and used to generate structural, mechanical and cell function indices that correspond to statistically significant representations of characteristics of tissue associated with such population.

Referring now to FIG. 1, there is a flow diagram of a method 1000 for profiling samples of normal tissue specimens. In step 50, a tissue type is selected for analysis. The tissue type corresponds to a population of tissue subject having shared characteristics. For example, the tissue type corresponds to human lung tissue, intestine tissue, cartilage tissue, etc. In addition, the tissue type may be further specified as a population of subjects having a common age bracket, race and/or gender. Thus, for example, the tissue type selected for analysis may correspond to a population of lung tissue subjects associated with Caucasian males between the ages of 18–35. The tissue type selected for analysis can correspond to either a normal or an abnormal tissue type. Moreover, in addition to human tissue, the tissue type selected for analysis may correspond to a tissue type associated with a particular plant or animal species, or a food product.

In step 100, a sample of specimens is selected from the population selected for analysis in step 50. The sample of specimens represents a subset of the selected population and includes a sufficient number of specimens to permit a statistically significant analysis of the population as a whole. Thus, the sample includes a sufficient number of specimens such that the structural, mechanical and cell function indices generated from the sample correspond to a statistically significant representation of those indices for the population as a whole.

In step 200, a plurality of structural indices representative of the selected population are measured from the sample and stored in a database. The structural indices are parameters that are representative of the physical structure of the tissue specimens in the sample. Exemplary structural indices measured and stored in step 200 include: the average density of each of a plurality of cell types in the specimens in the sample, an index of dispersion (e.g., standard deviation) associated with each measured average cell density, the average density of each of the matrix in the specimens in the sample, an index of dispersion associated with the measured average matrix density, the average layer thickness of each layer in the specimens in the sample, an index of dispersion associated with each measured average layer thickness, the average density of blood vessels in the specimens in the sample, an index of dispersion associated with the measured average blood vessel density, the average relative location of (or distance between) selected types of cells in the specimens in the sample, an index of dispersion associated with each measured average relative location of cell types, the average relative location between blood vessels and selected cell types in the specimens in the sample, and an index of dispersion associated with each measured average relative location between blood vessels and a selected cell type. It will be understood by those skilled in the art that structural indices other than those enumerated above may be measured and stored in step 200, and that the use of such other structural indices is within the scope of the present invention. A set of exemplary steps that may be used to measure a sample of specimens and generate the structural indices enumerated above is shown in detail in FIGS. 2, 2A and 2B and discussed more fully below.

Referring still to FIG. 1, in step 300, a plurality of mechanical indices representative of the selected population are measured from the sample and stored in the database. The mechanical indices are parameters that are representative of the reaction of the tissue specimens in the sample to external forces. Exemplary mechanical indices measured and stored in step 300 include: the average elasticity of specimens in the sample, an index of dispersion associated with the measured average elasticity, the average breaking strength of specimens in the sample, and an index of dispersion associated with the measured average breaking strength. It will be understood by those skilled in the art that mechanical indices other than those enumerated above may be measured and stored in step 300, and that the use of such other mechanical indices is within the scope of the present invention. A set of exemplary steps that may be used to measure a sample of specimens and generate the mechanical indices enumerated above is shown in detail in FIG. 3 and discussed more fully below.

In step 400, a plurality of cell function indices representative of the selected population are measured from the sample, stored in a database and optionally used to form a cell function map representative of the selected population. The cell function indices are parameters that represent the character and function of cells in the tissue specimens in the sample. Exemplary cell function indices measured and stored in step 400 include: the average amount of a first type of DNA in the specimens in the sample and an index of dispersion associated with the measured average amount of the first type of DNA, the average amount of a second type of DNA in the specimens in the sample and an index of dispersion associated with the measured average amount of the second type of DNA, . . . , the average amount of an nth type of DNA in the specimens in the sample and an index of dispersion associated with the measured average amount of the nth type of DNA; the average amount of a first type of mRNA in the specimens in the sample and an index of dispersion associated with the measured average amount of the first type of mRNA, the average amount of a second type of mRNA in the specimens in the sample and an index of dispersion associated with the measured average amount of the second type of mRNA, . . . , the average amount of an nth type of mRNA in the specimens in the sample and an index of dispersion associated with the measured average amount of the nth type of mRNA; the average amount of a first type of cellular protein in the specimens in the sample and an index of dispersion associated with the measured average amount of the first type of cellular protein, the average amount of a second type of cellular protein in the specimens in the sample and an index of dispersion associated with the measured average amount of the second type of cellular protein, . . . , the average amount of an nth type of cellular protein in the specimens in the sample and an index of dispersion associated with the measured average amount of the nth type of cellular protein; the average amount of a first type of cellular lipid in the specimens in the sample and an index of dispersion associated with the measured average amount of the first type of cellular lipid, the average amount of a second type of cellular lipid in the specimens in the sample and an index of dispersion associated with the measured average amount of the second type of cellular lipid, . . . , the average amount of an nth type of cellular lipid in the specimens in the sample and an index of dispersion associated with the measured average amount of the nth type of cellular lipid; and the average amount of a first type of ion distribution in the specimens in the sample and an index of dispersion associated with the measured average amount of the first type of ion distribution, the average amount of a second type of ion distribution in the specimens in the sample and an index of dispersion associated with the measured average amount of the second type of ion distribution, . . . , the average amount of an nth type of ion distribution in the specimens in the sample and an index of dispersion associated with the measured average amount of the nth type of ion distribution. It will be understood by those skilled in the art that cell function indices other than those enumerated above may be measured and stored in step 400, and that the use of such other structural indices is within the scope of the present invention. A set of exemplary steps that may be used to measure a sample of specimens and generate the cell function indices enumerated above is shown in detail in FIG. 4 and discussed more fully below.

In step 500, correlation operations are performed on the various structural, mechanical and cell function indices generated in steps 200, 300 and 400, and the results of the correlation operations are stored in the data base. Thus, in this step, selected pairs of structural indices are correlated with each other, selected pairs of mechanical indices are correlated with each other, selected pairs of cell function indices are correlated with each other, selected structural indices may be correlated with selected mechanical or cell function indices, and selected mechanical indices may be correlated with selected cell function indices. In one embodiment, correlations between the following pairs of indices are performed in step 500 and stored in the data base:

TABLE I

| Correlation Operation No. | Indices Being Correlated |
| --- | --- |
| 1 | Cell Density and Elasticity |
| 2 | Blood Vessel Density and Cell Density |
| 3 | Matrix Density and Breaking Strength |
| 4 | Blood Vessel Location and Density of Adjacent Cells |
| 5 | Layer Thickness and Cell Density |

It will be understood by those skilled in the art that correlation values other than those enumerated above may be measured and stored in step 500, and that the use of such other correlation values is within the scope of the present invention.

Figure 10:
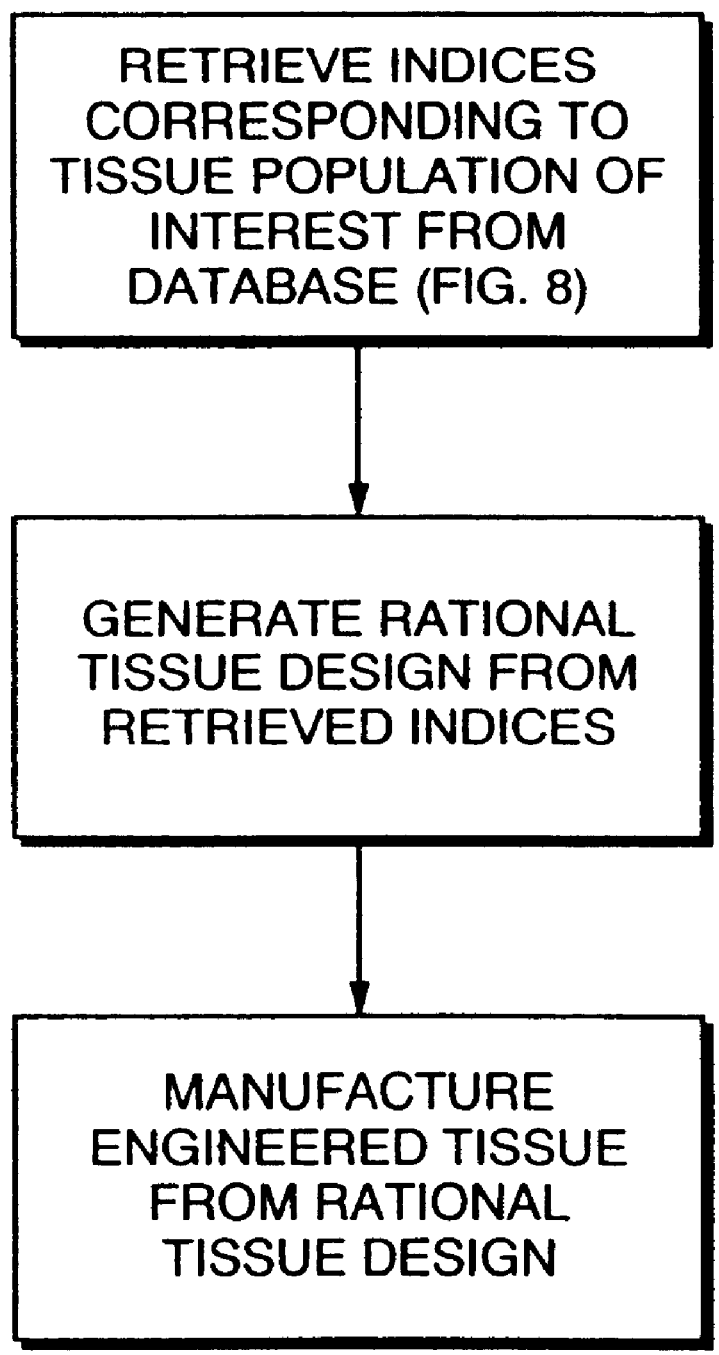
FIG. 10 is a flow diagram showing a method for designing and manufacturing engineered tissue, in accordance with a preferred embodiment of the present invention.

As shown in step 600, the process described above may be repeated for each tissue population of interest. By repeating this process for each population of interest, the present invention may be used to generate a data base such as that shown in FIG. 8, which includes structural, mechanical and cell function indices for many different tissue populations. The structural, mechanical and/or cell function indices associated with each tissue population collectively represent a "blueprint" of the tissue in the population and may be used, inter alia to rationally design and then manufacture engineered tissue corresponding to the tissue population (as shown in FIG. 10). The rational tissue design formed for a given tissue population using the present invention preferably consists of Cartesian coordinates of cells, matrices and blood vessels within units that repeat in a common fashion throughout the design. The coordinates are preferably in two-dimensions or three-dimensions. In a further embodiment, a fourth dimension (corresponding to time) may be included in the tissue design to account for changes to a particular tissue population as it ages over time. Thus, in one example, the time dimension in the tissue design might reflect the differences among the lung tissue of Caucasian males falling in different age brackets (e.g., 18–25 years old, 26–35 years old, etc.).

Figure 2A:
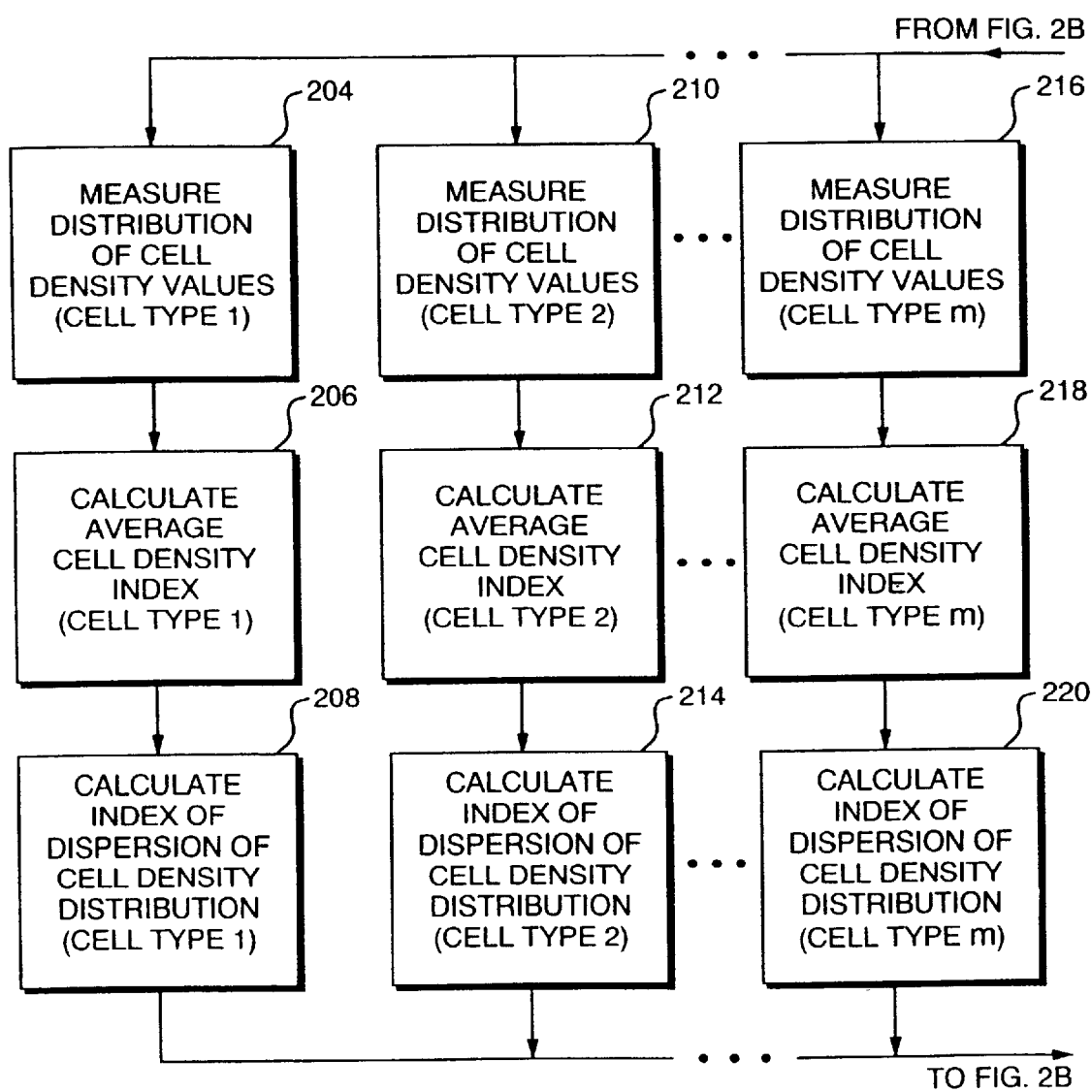
FIGS. 2A–2D are a flow diagram of a method for profiling a sample of normal tissue specimens obtained from a subset of a population of subjects with shared characteristics in order to generate a plurality of structural indices that correspond to statistically significant representations of characteristics of tissue associated with the population.
Figure 2B:
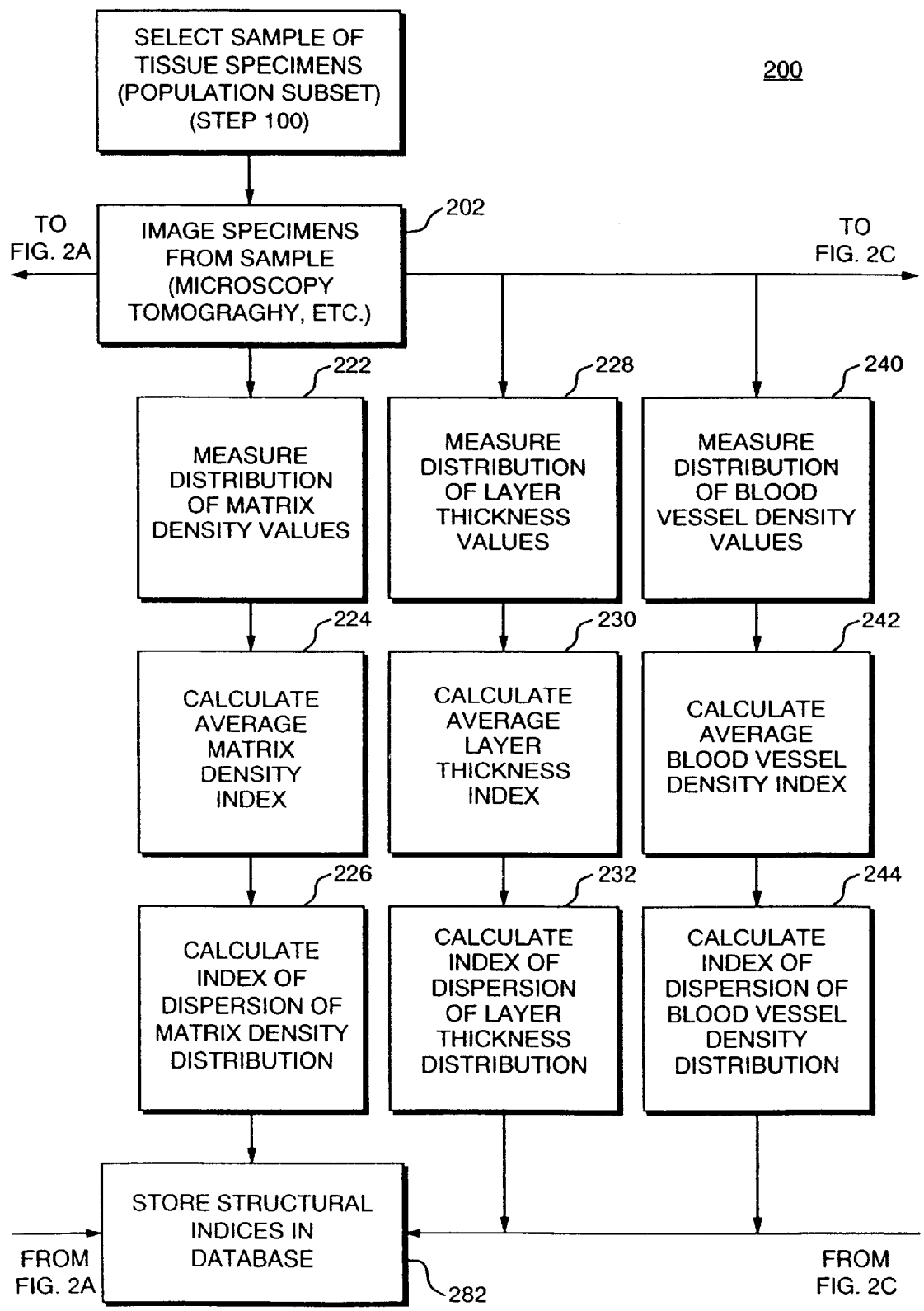
Figure 2C:
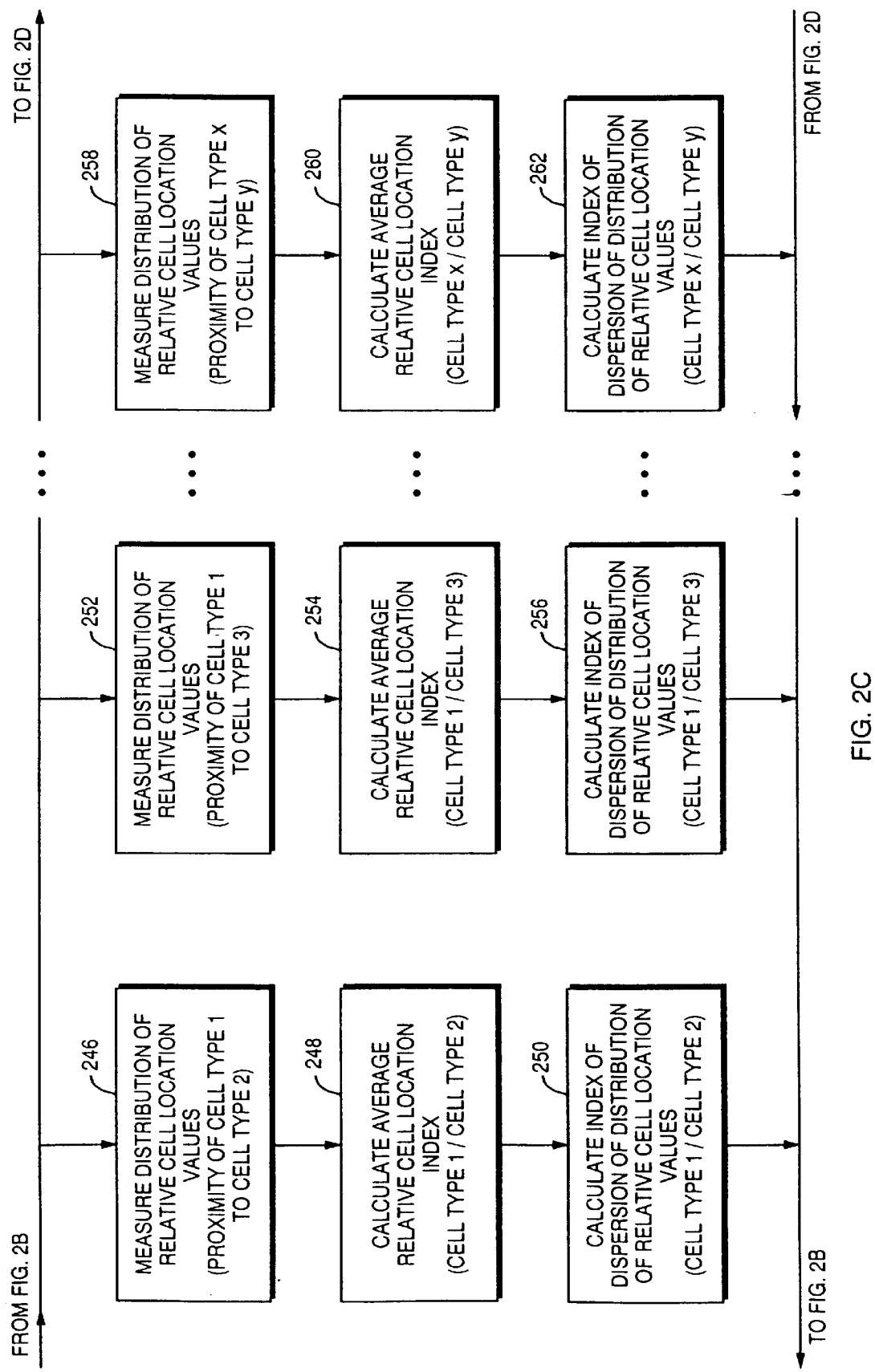
Figure 2D:
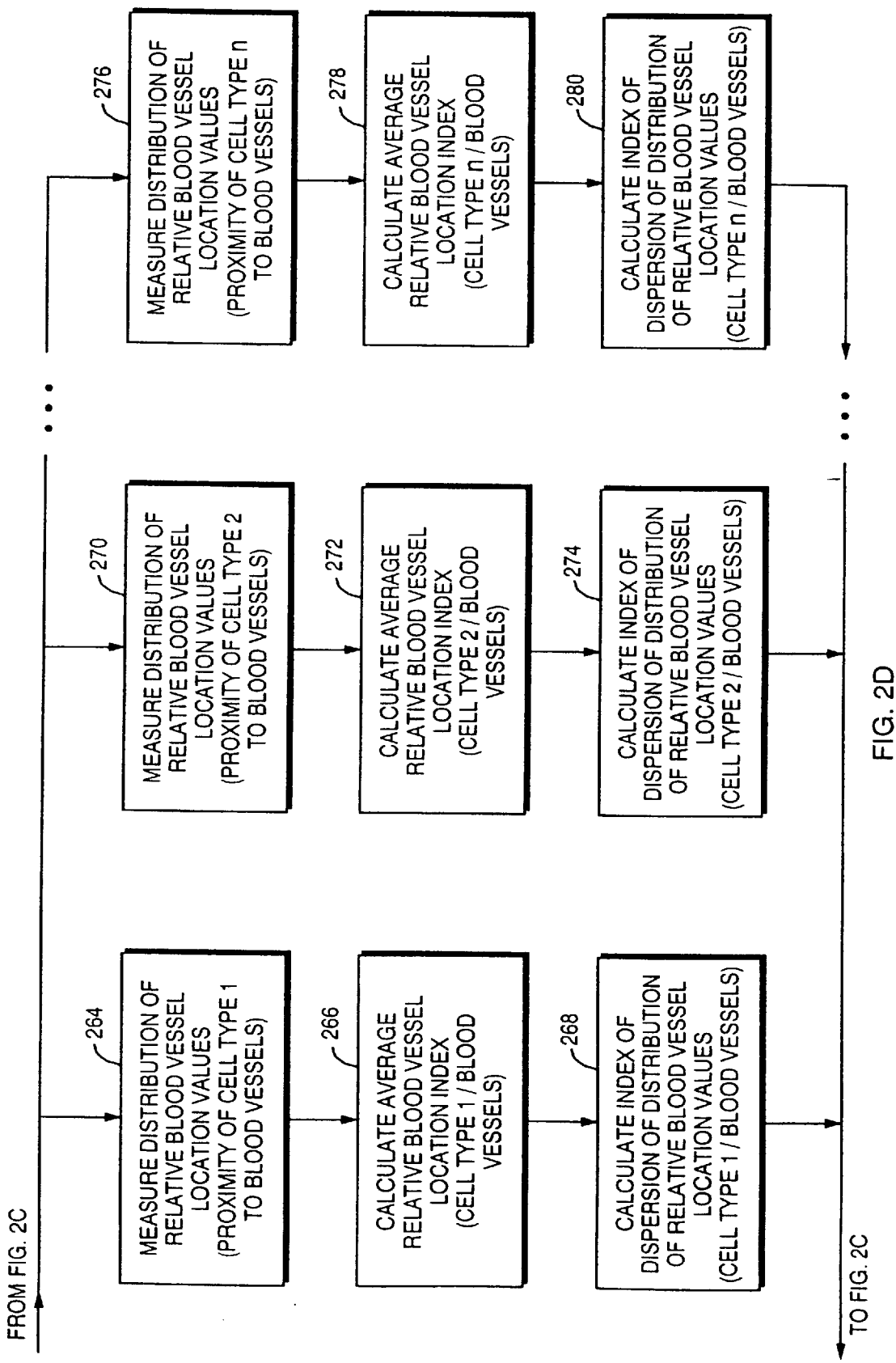

Referring now to FIGS. 2, 2A and 2B, there is shown a flow diagram of method 200 for profiling a sample of normal tissue specimens obtained from a subset of a population of subjects with shared characteristics in order to generate a plurality of structural indices that correspond to statistically significant representations of characteristics of tissue associated with the population. In step 202, each specimen from the sample selected in step 100 is imaged using, for example, light microscopy, fluorescent microscopy, spectral microscopy, hyper-spectral microscopy, electron microscopy, confocal microscopy and/or optical coherence tomography. Alternatively, the specimens from the samples may be imaged using a combination of the above imaging modalities. In one embodiment, a plurality of sections in each tissue specimen in the sample is imaged using one or more of the above imaging modalities in step 202.

In step 204, the imaging information from step 202 is analyzed in order to generate a distribution of density values associated with a particular cell type (i.e., cell type 1) in the specimens in the sample. For example, the imaging information corresponding to each imaged section of each specimen is analyzed in order to determine the density of the particular cell type (i.e., cell type 1) in the section. By performing such an analysis on each section of each specimen in the sample, a distribution of density values for the particular cell type may then be obtained. In step 206, an average cell density index representative of an average density of the particular cell type (i.e., cell type 1) in the population is calculated by taking the statistical average of the distribution of values generated in step 204. The statistical average corresponds, for example, to a mean, median or mode of the distribution of values generated in step 204. In step 208, an index of dispersion about the average density of the particular cell type (i.e., cell type 1) in the population is calculated by, for example, taking the standard deviation, standard error, or standard error of the mean of the distribution of values generated in step 204.

In step 210, the imaging information from step 202 may be further analyzed in order to generate a further distribution of density values associated with a different cell type (i.e., cell type 2) in the specimens in the sample. Again, the imaging information corresponding to each imaged section of each specimen is analyzed in order to determine the density of the particular cell type (i.e., cell type 2) in the section. By performing such an analysis on each section of each specimen in the sample, a distribution of density values for the particular cell type (i.e., cell type 2) is then obtained. In step 212, an average cell density index representative of an average density of the particular cell type (i.e., cell type 2) in the population is calculated by taking the statistical average of the distribution of values generated in step 210. Again, the statistical average corresponds, for example, to a mean, median or mode of the distribution of values generated in step 210. In step 212, an index of dispersion about the average density of the particular cell type (i.e., cell type 2) in the population is calculated by, for example, taking the standard deviation, standard error, or standard error of the mean of the distribution of values generated in step 210.

As shown in steps 216, 218, 220, steps 204, 206, 208 and 210, 212, 214 may be repeated further times for each other cell type of interest in order to generate an average cell density index and a corresponding index of dispersion for each cell type of interest in the population.

In step 222, the imaging information from step 202 is analyzed in order to generate a distribution of density values associated with the matrix associated with the specimens in the sample. Here, the imaging information corresponding to each imaged section of each specimen is analyzed in order to determine the density of the matrix in the section. This matrix density in a given specimen may correspond, for example, to the density of one or more proteins in the extra-cellular matrix of the specimen. By performing such an analysis on each section of each specimen in the sample, a distribution of density values for the particular matrix is obtained. In step 224, an average matrix density index representative of an average density of the particular matrix associated with the population is calculated by taking the statistical average of the distribution of values generated in step 222. The statistical average corresponds, for example, to a mean, median or mode of the distribution of values generated in step 222. In step 226, an index of dispersion about the average density of the particular matrix associated with the population is calculated by, for example, taking the standard deviation, standard error, or standard error of the mean of the distribution of values generated in step 222.

In step 228, the imaging information from step 202 is analyzed in order to generate a distribution of layer thickness values associated with the specimens in the sample. Here, the imaging information corresponding to each imaged section of each specimen is analyzed in order to determine the thickness a particular tissue layer in the section. By performing such an analysis on each section of each specimen in the sample, a distribution of layer thickness values for the particular layer is obtained. In step 230, an average layer thickness index representative of an average thickness of the particular tissue layer associated with the population is calculated by taking the statistical average of the distribution of values generated in step 228. The statistical average corresponds, for example, to a mean, median or mode of the distribution of values generated in step 228. In step 232, an index of dispersion about the average layer thickness of the particular layer associated with the population is calculated by, for example, taking the standard deviation, standard error, or standard error of the mean of the distribution of values generated in step 228. For tissue populations with multiple layers, steps 228–232 are preferably repeated for each tissue layer of interest, and an average layer thickness index and an index of dispersion about such average are generated for each such layer. In addition, in cases where a tissue population has multiple layers, the other structural, mechanical and cell function indices described herein may be determined separately for each tissue layer in the population.

In step 240, the imaging information from step 202 is analyzed in order to generate a distribution of density values associated with blood vessels in the specimens in the sample. Here, the imaging information corresponding to each imaged section of each specimen is analyzed in order to determine the density of blood vessels in the section. In performing this analysis, the blood vessels can be categorized by diameter, and the density of blood vessels in a given specimen can correspond to the density of blood vessels having one diameter. Alternatively, the density of blood vessels in a given specimen will correspond to the density of all blood vessels (regardless of their diameter) in the specimen. By performing such an analysis on each section of each specimen in the sample, a distribution of blood vessel density values is obtained. In step 242, an average blood vessel density index representative of an average density of blood vessels (i.e., blood vessels per unit area/unit volume) in the population is calculated by taking the statistical average (e.g., mean, median or mode) of the distribution of values generated in step 240. In step 244, an index of dispersion about the average blood vessel density is calculated by, for example, taking the standard deviation, standard error, or standard error of the mean of the distribution of values generated in step 240.

In step 246, the imaging information from step 202 is further analyzed in order to generate a distribution of relative cell location values representative of the relative proximity of two particular cell types (i.e., cell types 1 and 2) in the specimens in the sample. For example, the imaging information corresponding to each imaged section of each specimen is analyzed in order to determine the average proximity of the two particular cell types (i.e., cell types 1 and 2) in the section. This process can be performed by using image analysis to determine the centers and boundaries of the cell types of interest, and then calculating the distances between the relevant cells in each image. For example, in cases where cells of type 1 are intermixed with cells of type 2, each occurrence of cell type 1 in a section can be identified and the distance to the closest cell of type 2 can then be measured. Alternatively, in cases where cells of type 1 are located in a space that is typically distinct from that occupied by cells of type 2, the centroids of the respective spaces occupied by the cells of type 1 and the cells of type 2 can be determined, and the distance between the centroids can then be measured. By performing such an analysis on each section of each specimen in the sample, a distribution of relative cell location values for the particular cell types of interest may then be obtained. In step 248, an average relative cell location index representative of an average proximity between the particular cell types of interest (i.e., cell types 1 and 2) in the population is calculated by taking the statistical average (e.g., mean, median or mode) of the distribution of values generated in step 246. In step 250, an index of dispersion about the average proximity between the particular cell types of interest (i.e., cell types 1 and 2) in the population is calculated by, for example, taking the standard deviation, standard error, or standard error of the mean of the distribution of values generated in step 246.

In step 252, the imaging information from step 202 is further analyzed in order to generate a distribution of relative cell location values representative of the relative proximity of a further pair of particular cell types (i.e., cell types 1 and 3) in the specimens in the sample. For example, the imaging information corresponding to each imaged section of each specimen is analyzed (as discussed in connection with step 246) in order to determine the average proximity of the a different pair of particular cell types (i.e., cell types 1 and 3) in the section. By performing such an analysis on each section of each specimen in the sample, a distribution of relative cell location values for the particular cell types of interest may then be obtained. In step 254, an average relative cell location index representative of an average proximity between the particular cell types of interest (i.e., cell types 1 and 3) in the population is calculated by taking the statistical average (e.g., mean, median or mode) of the distribution of values generated in step 252. In step 256, an index of dispersion about the average proximity between the particular cell types of interest (i.e., cell types 1 and 3) in the population is calculated by, for example, taking the standard deviation, standard error, or standard error of the mean of the distribution of values generated in step 252.

As shown in steps 258, 260, 262, steps 246, 248, 250 and 252, 254, 256 may be repeated further times for each other pair of cell types of interest (i.e., cell types a and b) in order to generate an average relative cell location index and a corresponding index of dispersion for each pair of cell types of interest in the population.

In step 264, the imaging information from step 202 is further analyzed in order to generate a distribution of relative blood vessel location values representative of the relative proximity of blood vessel to a particular type of cell (i.e., cell types 1) in the specimens in the sample. For example, the imaging information corresponding to each imaged section of each specimen is analyzed in order to determine the average proximity of blood vessels to the particular cell type (i.e., cell types 1) in the section. This process can be performed by using image analysis to determine the centers and boundaries of the cell types of interest, and then calculating the distances between the relevant cells in each image and the closest blood vessels. By performing such an analysis on each section of each specimen in the sample, a distribution of relative blood vessel location values for the particular cell type of interest may then be obtained. In step 266, an average relative blood vessel location index representative of an average proximity between blood vessels and the particular cell type of interest (i.e., cell type 1) in the population is calculated by taking the statistical average (e.g., mean, median or mode) of the distribution of values generated in step 264. In step 268, an index of dispersion about the average proximity between blood vessels and the particular cell type of interest (i.e., cell type 1) in the population is calculated by, for example, taking the standard deviation, standard error, or standard error of the mean of the distribution of values generated in step 264.

In step 270, the imaging information from step 202 is further analyzed in order to generate a distribution of relative blood vessel location values representative of the relative proximity between blood vessel of a further particular cell type of interest (i.e., cell type 2) in the specimens in the sample. For example, the imaging information corresponding to each imaged section of each specimen is analyzed in order to determine the average proximity of blood vessels to the further particular cell type (i.e., cell type 2) in the section. This process can be performed by using image analysis to determine the centers and boundaries of the cell types of interest, and then calculating the distances between the relevant cells in each image and the closest blood vessels. By performing such an analysis on each section of each specimen in the sample, a distribution of relative blood vessel location values for the particular cell type of interest may then be obtained. In step 272, an average relative blood vessel location index representative of an average proximity between blood vessels and the cell type of interest (i.e., cell type 2) in the population is calculated by taking the statistical average (e.g., mean, median or mode) of the distribution of values generated in step 270. In step 274, an index of dispersion about the average proximity between blood vessel and the cell type of interest (i.e., cell type 2) in the population is calculated by, for example, taking the standard deviation, standard error, or standard error of the mean of the distribution of values generated in step 270.

As shown in steps 276, 278, 280, steps 264, 266, 268 and 270, 272, 274 may be repeated further times for other cell types of interest (i.e., up to cell type n) in order to generate an average relative blood vessel location index and a corresponding index of dispersion for each cell type of interest in the population.

In step 282, all of the structural indices associated with the population of interest and described above are stored in a tissue data base using, for example, a data structure such as that shown in FIG. 5. For tissue populations having multiple layers, a separate data structure of the form shown in FIG. 5 may be generated for each layer of interest.

Figure 3:
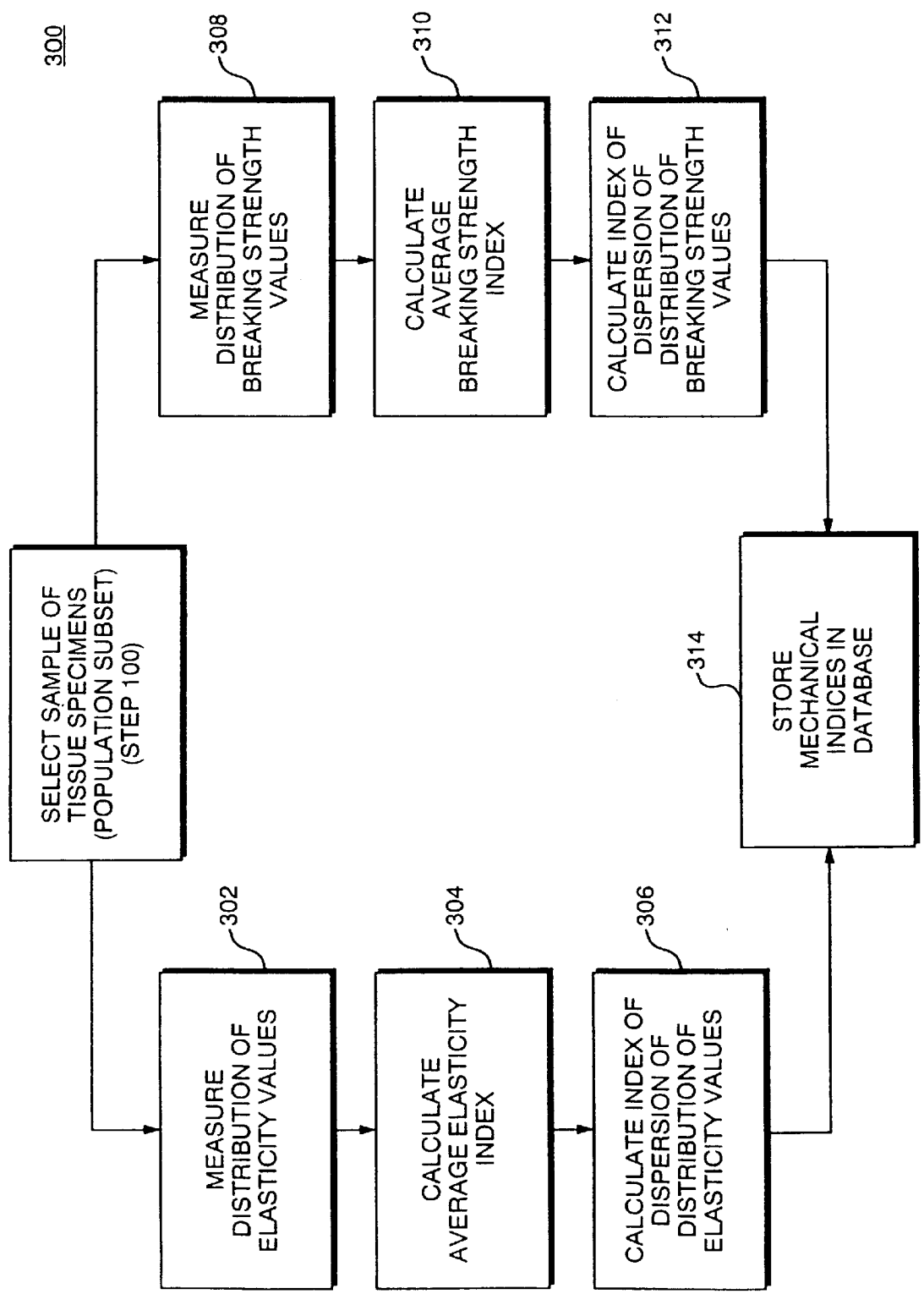
FIG. 3 is a flow diagram of a method for profiling a sample of normal tissue specimens obtained from a subset of a population of subjects with shared characteristics in order to generate a plurality of mechanical indices that correspond to statistically significant representations of characteristics of tissue associated with the population.

Referring now to FIG. 3, there is shown a flow diagram of method 300 for profiling a sample of normal tissue specimens obtained from a subset of a population of subjects with shared characteristics in order to generate a plurality of mechanical indices that correspond to statistically significant representations of characteristics of tissue associated with the population. In method 300, mechanical tests such as, for example, tensile strength and mechanical elasticity tests, are applied to each specimen from the sample selected in step 100. In one embodiment, the mechanical tests may be applied to a plurality of sections in each tissue specimen in the sample.

In step 302, the information from the mechanical tests is analyzed in order to generate a distribution of elasticity values associated with the specimens in the sample. For example, the mechanical information corresponding to each analyzed section of each specimen is analyzed in order to determine the elasticity of the particular section. By performing such an analysis on each section of each specimen in the sample, a distribution of elasticity values for the population may then be obtained. In step 304, an average elasticity index representative of an average elasticity of the population is calculated by taking the statistical average (e.g., mean, median or mode) of the distribution of values generated in step 302. In step 306, an index of dispersion about the average elasticity of the population is calculated by, for example, taking the standard deviation, standard error, or standard error of the mean of the distribution of values generated in step 302.

In step 308, the information from the mechanical tests is analyzed in order to generate a distribution of breaking strength values associated with the specimens in the sample. For example, the mechanical information corresponding to each analyzed section of each specimen is analyzed in order to determine the breaking strength of the particular section. By performing such an analysis on each section of each specimen in the sample, a distribution of breaking strength values for the population may then be obtained. In step 310, an average breaking strength index representative of an average breaking strength of the population is calculated by taking the statistical average (e.g., mean, median or mode) of the distribution of values generated in step 308. In step 312, an index of dispersion about the average breaking strength of the population is calculated by, for example, taking the standard deviation, standard error, or standard error of the mean of the distribution of values generated in step 308.

In step 314, all of the mechanical indices associated with the population of interest and described above are stored in a tissue data base using, for example, a data structure such as that shown in FIG. 6. For tissue populations having multiple layers, a separate data structure of the form shown in FIG. 6 may be generated for each layer of interest.

Figure 4A:
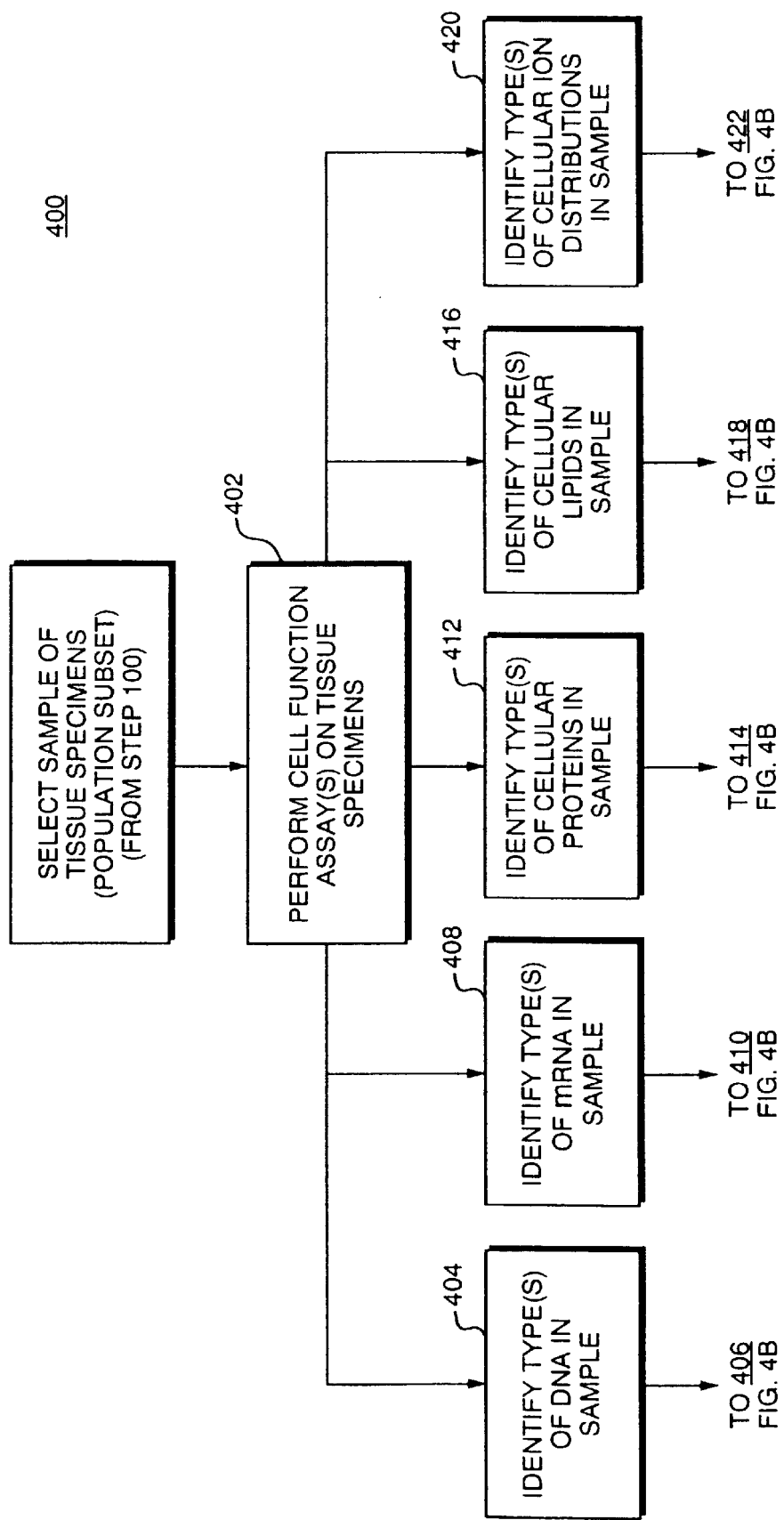
FIGS. 4A–4B are a flow diagram of a method for profiling a sample of normal tissue specimens obtained from a subset of a population of subjects with shared characteristics in order to generate a plurality of cell function indices that correspond to statistically significant representations of characteristics of tissue associated with the population.
Figure 4B:
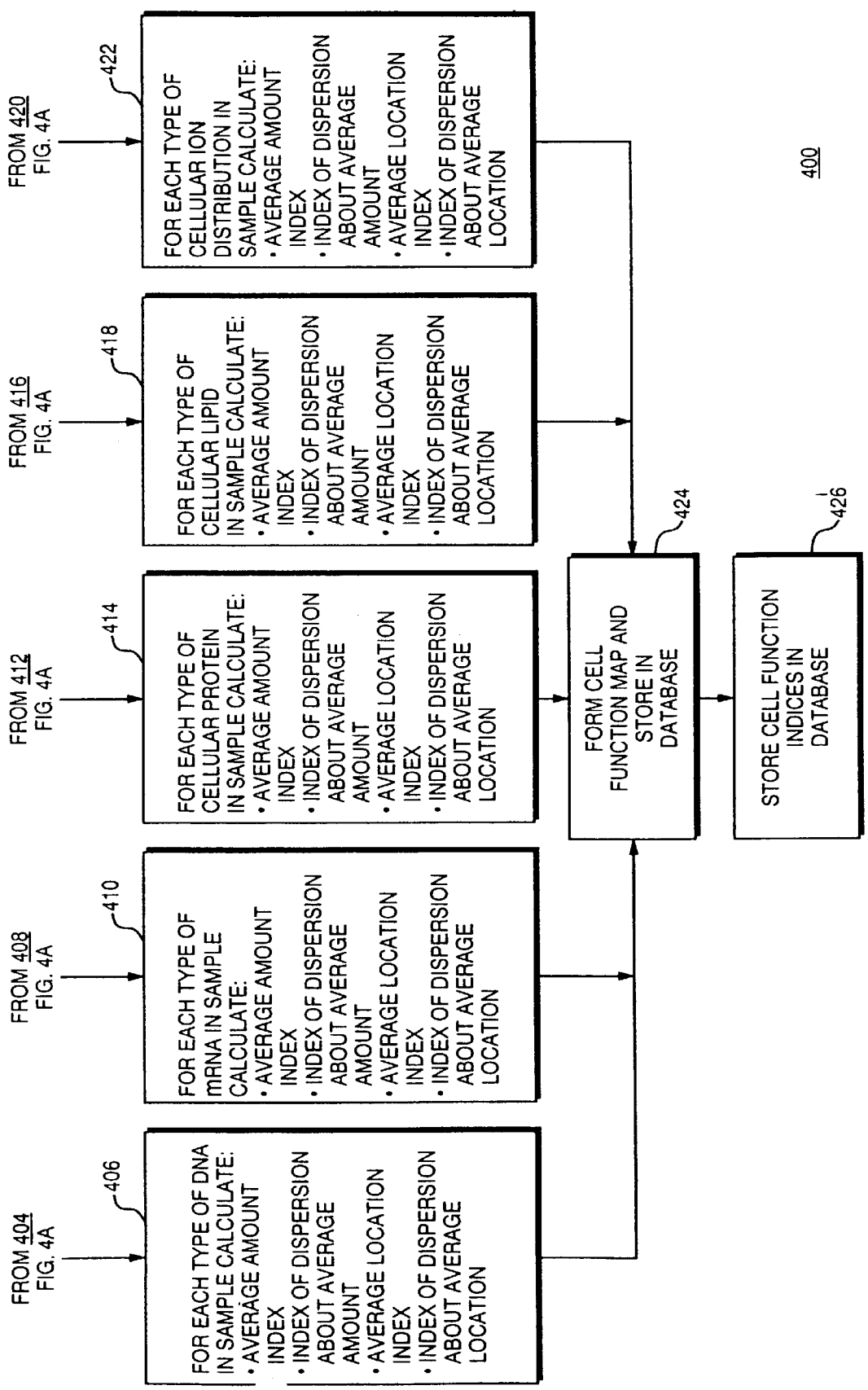

Referring now to FIG. 4, there is shown a flow diagram of method 400 for profiling a sample of normal tissue specimens obtained from a subset of a population of subjects with shared characteristics in order to generate a plurality of cell function indices that correspond to statistically significant representations of characteristics of tissue associated with the population. In step 402, a cell function assay is applied to each specimen from the sample selected in step 100. The cell function assay(s) that may be used for a given tissue population include, for example, DNA content, mRNA content, protein content, ion content, lipid content, and their respective individual elements such specific genes, specific mRNA, specific proteins, specific ions, and specific lipid content assays. In one embodiment, one or more assays are applied to a plurality of sections in each tissue specimen in the sample.

In step 404, the cell function information from step 402 is analyzed in order to identify types of DNA that are present in the specimens in the sample. The types of DNA identified for analysis preferably correspond to the types of DNA that distinguish the tissue population of interest from other tissue populations. In step 406, four cell function indices are determined for each type of DNA that was identified in step 404. More particularly, for each identified type of DNA, the following indices are determined in step 404: (i) the average amount of the particular type of DNA in the specimens in the sample, (ii) an index of dispersion associated with the measured average amount of the particular type of DNA, (iii) the average relative location of the particular type of DNA in the specimens in the sample, and (iv) an index of dispersion associated with the measured average relative location of the particular type of DNA.

Referring still to step 406, for each identified type of DNA, the average amount of the particular type of DNA in the specimens in the sample and the index of dispersion associated with the measured average amount of the particular type of DNA are determined by first analyzing the cell function information corresponding to each section of each specimen in the sample in order to determine the average amount of the particular type of DNA in each such section. By performing such an analysis on each section of each specimen in the sample, a distribution of DNA amount values for the particular type of DNA may then be obtained.

An average amount index representative of an average amount of the particular type of DNA in the population is then calculated by taking the statistical average of this distribution. Similarly, an index of dispersion about the average amount of the particular type of DNA in the population is calculated by, for example, taking the standard deviation, standard error, or standard error of the mean of the distribution of DNA amount values obtained for the particular type of DNA from the sample.

Referring still to step 406, for each identified type of DNA, the average relative location of the particular type of DNA in the specimens in the sample and the index of dispersion associated with the measured average relative location of the particular type of DNA are determined by first analyzing the cell function information corresponding to each section of each specimen in the sample in order to determine the average relative location of the particular type of DNA in each such section. By performing such an analysis on each section of each specimen in the sample, a distribution of DNA relative location values for the particular type of DNA may then be obtained. An average relative location index representative of an average relative location of the particular type of DNA in the population is then calculated by taking the statistical average of this distribution. Similarly, an index of dispersion about the average relative location of the particular type of DNA in the population is calculated by, for example, taking the standard deviation, standard error, or standard error of the mean of the distribution of DNA relative location values obtained for the particular type of DNA from the sample.

In step 408, the cell function information from step 402 is analyzed in order to identify types of mRNA that are present in the specimens in the sample. The types of mRNA identified for analysis preferably correspond to the types of mRNA that distinguish the tissue population of interest from other tissue populations. In step 410, four cell function indices are determined for each type of mRNA that was identified in step 408. More particularly, for each identified type of mRNA, the following indices are determined in step 410: (i) the average amount of the particular type of mRNA in the specimens in the sample, (ii) an index of dispersion associated with the measured average amount of the particular type of mRNA, (iii) the average relative location of the particular type of mRNA in the specimens in the sample, and (iv) an index of dispersion associated with the measured average relative location of the particular type of mRNA.

Referring still to step 410, for each identified type of mRNA, the average amount of the particular type of mRNA in the specimens in the sample and the index of dispersion associated with the measured average amount of the particular type of mRNA are determined by first analyzing the cell function information corresponding to each section of each specimen in the sample in order to determine the average amount of the particular type of mRNA in each such section. By performing such an analysis on each section of each specimen in the sample, a distribution of mRNA amount values for the particular type of mRNA may then be obtained. An average amount index representative of an average amount of the particular type of mRNA in the population is then calculated by taking the statistical average of this distribution. Similarly, an index of dispersion about the average amount of the particular type of mRNA in the population is calculated by, for example, taking the standard deviation, standard error, or standard error of the mean of the distribution of mRNA amount values obtained for the particular type of mRNA from the sample.

Referring still to step 410, for each identified type of mRNA, the average relative location of the particular type of mRNA in the specimens in the sample and the index of dispersion associated with the measured average relative location of the particular type of mRNA are determined by first analyzing the cell function information corresponding to each section of each specimen in the sample in order to determine the average relative location of the particular type of mRNA in each such section. By performing such an analysis on each section of each specimen in the sample, a distribution of mRNA relative location values for the particular type of mRNA may then be obtained. An average relative location index representative of an average relative location of the particular type of mRNA in the population is then calculated by taking the statistical average of this distribution. Similarly, an index of dispersion about the average relative location of the particular type of mRNA in the population is calculated by, for example, taking the standard deviation, standard error, or standard error of the mean of the distribution of mRNA relative location values obtained for the particular type of mRNA from the sample.

In step 412, the cell function information from step 402 is analyzed in order to identify types of cellular proteins that are present in the specimens in the sample. The types of cellular proteins identified for analysis preferably correspond to the types of cellular proteins that distinguish the tissue population of interest from other tissue populations. In step 414, four cell function indices are determined for each type of cellular protein that was identified in step 412. More particularly, for each identified type of cellular protein, the following indices are determined in step 414: (i) the average amount of the particular type of cellular protein in the specimens in the sample, (ii) an index of dispersion associated with the measured average amount of the particular type of cellular protein, (iii) the average relative location of the particular type of cellular protein in the specimens in the sample, and (iv) an index of dispersion associated with the measured average relative location of the particular type of cellular protein.

Referring still to step 414, for each identified type of cellular protein, the average amount of the particular type of cellular protein in the specimens in the sample and the index of dispersion associated with the measured average amount of the particular type of cellular protein are determined by first analyzing the cell function information corresponding to each section of each specimen in the sample in order to determine the average amount of the particular type of cellular protein in each such section. By performing such an analysis on each section of each specimen in the sample, a distribution of cellular protein amount values for the particular type of cellular protein may then be obtained. An average amount index representative of an average amount of the particular type of cellular protein in the population is then calculated by taking the statistical average of this distribution. Similarly, an index of dispersion about the average amount of the particular type of cellular protein in the population is calculated by, for example, taking the standard deviation, standard error, or standard error of the mean of the distribution of cellular protein amount values obtained for the particular type of cellular protein from the sample.

Referring still to step 414, for each identified type of cellular protein, the average relative location of the particular type of cellular protein in the specimens in the sample and the index of dispersion associated with the measured average relative location of the particular type of cellular protein are determined by first analyzing the cell function information corresponding to each section of each specimen in the sample in order to determine the average relative location of the particular type of cellular protein in each such section. By performing such an analysis on each section of each specimen in the sample, a distribution of cellular protein relative location values for the particular type of cellular protein may then be obtained. An average relative location index representative of an average relative location of the particular type of cellular protein in the population is then calculated by taking the statistical average of this distribution. Similarly, an index of dispersion about the average relative location of the particular type of cellular protein in the population is calculated by, for example, taking the standard deviation, standard error, or standard error of the mean of the distribution of cellular protein relative location values obtained for the particular type of cellular protein from the sample.

In step 416, the cell function information from step 402 is analyzed in order to identify types of cellular lipids that are present in the specimens in the sample. The types of cellular lipids identified for analysis preferably correspond to the types of cellular lipids that distinguish the tissue population of interest from other tissue populations. In step 418, four cell function indices are determined for each type of cellular lipid that was identified in step 416. More particularly, for each identified type of cellular lipid, the following indices are determined in step 418: (i) the average amount of the particular type of cellular lipid in the specimens in the sample, (ii) an index of dispersion associated with the measured average amount of the particular type of cellular lipid, (iii) the average relative location of the particular type of cellular lipid in the specimens in the sample, and (iv) an index of dispersion associated with the measured average relative location of the particular type of cellular lipid.

Referring still to step 418, for each identified type of cellular lipid, the average amount of the particular type of cellular lipid in the specimens in the sample and the index of dispersion associated with the measured average amount of the particular type of cellular lipid are determined by first analyzing the cell function information corresponding to each section of each specimen in the sample in order to determine the average amount of the particular type of cellular lipid in each such section. By performing such an analysis on each section of each specimen in the sample, a distribution of cellular lipid amount values for the particular type of cellular lipid may then be obtained. An average amount index representative of an average amount of the particular type of cellular lipid in the population is then calculated by taking the statistical average of this distribution. Similarly, an index of dispersion about the average amount of the particular type of cellular lipid in the population is calculated by, for example, taking the standard deviation, standard error, or standard error of the mean of the distribution of cellular lipid amount values obtained for the particular type of cellular lipid from the sample.

Referring still to step 418, for each identified type of cellular lipid, the average relative location of the particular type of cellular lipid in the specimens in the sample and the index of dispersion associated with the measured average relative location of the particular type of cellular lipid are determined by first analyzing the cell function information corresponding to each section of each specimen in the sample in order to determine the average relative location of the particular type of cellular lipid in each such section. By performing such an analysis on each section of each specimen in the sample, a distribution of cellular lipid relative location values for the particular type of cellular lipid may then be obtained. An average relative location index representative of an average relative location of the particular type of cellular lipid in the population is then calculated by taking the statistical average of this distribution. Similarly, an index of dispersion about the average relative location of the particular type of cellular lipid in the population is calculated by, for example, taking the standard deviation, standard error, or standard error of the mean of the distribution of cellular lipid relative location values obtained for the particular type of cellular lipid from the sample.

In step 420, the cell function information from step 402 is analyzed in order to identify types of cellular ion distributions that are present in the specimens in the sample. The types of cellular ion distributions identified for analysis preferably correspond to the types of cellular ion distributions that distinguish the tissue population of interest from other tissue populations. In step 422, four cell function indices are determined for each type of cellular ion distribution that was identified in step 420. More particularly, for each identified type of cellular ion distribution, the following indices are determined in step 422: (i) the average amount of the particular type of cellular ion distribution in the specimens in the sample, (ii) an index of dispersion associated with the measured average amount of the particular type of cellular ion distribution, (iii) the average relative location of the particular type of cellular ion distribution in the specimens in the sample, and (iv) an index of dispersion associated with the measured average relative location of the particular type of cellular ion distribution.

Referring still to step 422, for each identified type of cellular ion distribution, the average amount of the particular type of cellular ion distribution in the specimens in the sample and the index of dispersion associated with the measured average amount of the particular type of cellular ion distribution are determined by first analyzing the cell function information corresponding to each section of each specimen in the sample in order to determine the average amount of the particular type of cellular ion distribution in each such section. By performing such an analysis on each section of each specimen in the sample, a sample distribution of cellular ion amount values for the particular type of cellular ion distribution may then be obtained. An average amount index representative of an average amount of the particular type of cellular ion distribution in the population is then calculated by taking the statistical average of the sample distribution. Similarly, an index of dispersion about the average amount of the particular type of cellular ion distribution in the population is calculated by, for example, taking the standard deviation, standard error, or standard error of the mean of the sample distribution.

Referring still to step 422, for each identified type of cellular ion distribution, the average relative location of the particular type of cellular ion distribution in the specimens in the sample and the index of dispersion associated with the measured average relative location of the particular type of cellular ion distribution are determined by first analyzing the cell function information corresponding to each section of each specimen in the sample in order to determine the average relative location of the particular type of cellular ion distribution in each such section. By performing such an analysis on each section of each specimen in the sample, a sample distribution of relative location values for the particular type of cellular ion distribution may then be obtained. An average relative location index representative of an average relative location of the particular type of cellular ion distribution in the population is then calculated by taking the statistical average of the sample distribution. Similarly, an index of dispersion about the average relative location of the particular type of cellular ion distribution in the population is calculated by, for example, taking the standard deviation, standard error, or standard error of the mean of the sample distribution.

Figure 9:
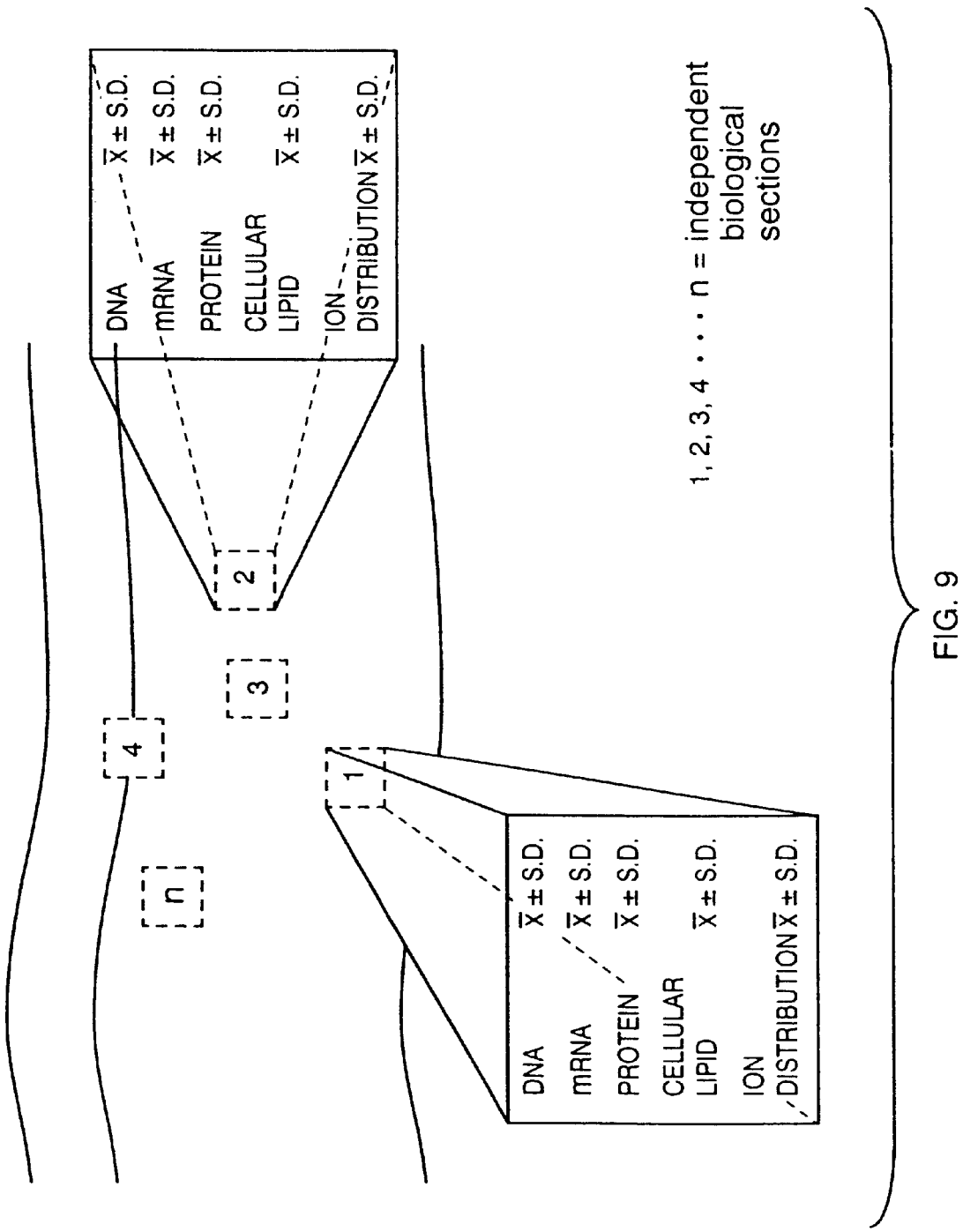
FIG. 9 is an exemplary cell function map associated with a tissue population and generated using the cell function indices described herein.

In step 424, the cell function indices associated with the population of interest and described above are optionally used to form a cell function map representative of the population of interest. An exemplary cell function map formed using such cell function indices is shown in FIG. 9. The cell function map is also preferably stored in the data base with the structural, mechanical and cell function indices associated with the population of interest.

In step 426, all of the cell function indices associated with the population of interest and described above are stored in a tissue data base using, for example, a data structure such as that shown in FIGS. 7, 7A, 7B. Again, for tissue populations having multiple layers, a separate data structure of the form shown in FIGS. 7, 7a, 7B may be generated for each layer of interest. The cell function map is also preferably stored in the data base with the cell function indices associated with the population of interest.

As mentioned above, process 1000 described above may be repeated for each tissue population of interest. By repeating this process for each population of interest, the present invention may be used to generate a data base such as that shown in FIG. 8, which includes structural, mechanical and cell function indices for many different tissue populations. The data base shown in FIG. 8 also optionally includes correlation values (as discussed above) and a cell function map for each population of interest.

In one embodiment, process 1000 is used to generate a database that includes structural, mechanical and cell function indices and optionally the correlation values and cell function map information discussed above for each of the following tissue populations: normal intestine tissue, normal cartilage tissue, normal eye tissue, normal bone tissue, normal fat tissue, normal muscle tissue, normal kidney tissue, normal brain tissue, normal heart tissue, normal liver tissue, normal skin tissue, normal pleura tissue, normal peritoneum tissue, normal pericardium tissue, normal dura-mater tissue, normal oral-nasal mucus membrane tissue, normal pancreas tissue, normal spleen tissue, normal gall bladder tissue, normal blood vessel tissue, normal bladder tissue, normal uterus tissue, normal ovarian tissue, normal urethra tissue, normal penile tissue, normal vaginal tissue, normal esophagus tissue, normal anus tissue, normal adrenal gland tissue, normal ligament tissue, normal intervertebral disk tissue, normal bursa tissue, normal meniscus tissue, normal fascia tissue, normal bone marrow tissue, normal tendon tissue, normal pulley tissue, normal tendon sheath tissue, normal lymph node tissue, or normal nerve tissue (e.g., normal motor nerve tissue, normal sensory nerve tissue, or normal autonomic nerve tissue.)

In a particularly preferred embodiment, process 1000 is used to generate a database that includes multiple sets of structural, mechanical and cell function indices and optionally the correlation values and cell function map information discussed above for each of the tissue types set forth in the paragraph above. In this embodiment, for each tissue type (e.g., normal lung tissue), multiple tissue populations are defined based on age bracket, race and/or gender. Thus, for example, a first normal lung tissue population will include lung tissue from Caucasian males between ages x-y; a second normal lung tissue population will include lung tissue from Asian males between ages x-y; a third normal lung tissue population will include lung tissue from Caucasian females between ages x-y; and so on. In this embodiment, a separate set of structural, mechanical and cell function indices and optionally the correlation values and cell function map information discussed above is determined using process 1000 for each of the different lung tissue populations and then stored in the tissue information database. In a still further embodiment, the different populations associated with a given tissue type may also be defined based on other criteria such as the physical fitness level, behavior, geographic location, nationality or disease(s) associated with the subjects having the given tissue type.

In accordance with still further aspects, process 1000 is used to generate a database that includes structural, mechanical and cell function indices and optionally the correlation values and cell function map information discussed above for populations of abnormal tissue types, for population of tissue types associated with specific plant or animal species, for populations of non-living tissue types and for populations of virtual tissue types.

In a still further embodiment, the present invention may used to profile "composite" tissue types, i.e., tissue populations that consist of two or more normal tissue types. In this further embodiment, the sample of normal tissue specimens profiled during process 1000 correspond to first and second groups of different normal tissue specimens, wherein the first and second groups each correspond, for example, to a set of either normal intestine tissue specimens, normal cartilage tissue specimens, normal eye tissue specimens, normal bone tissue specimens, normal fat tissue specimens, normal muscle tissue specimens, normal kidney tissue specimens, normal brain tissue specimens, normal heart tissue specimens, normal liver tissue specimens, normal skin tissue specimens, normal pleura tissue specimens, normal peritoneum tissue specimens, normal pericardium tissue specimens, normal dura-mater tissue specimens, normal oral-nasal mucus membrane tissue specimens, normal pancreas tissue specimens, normal spleen tissue specimens, normal gall bladder tissue specimens, normal blood vessel tissue specimens, normal bladder tissue specimens, normal uterus tissue specimens, normal ovarian tissue specimens, normal urethra tissue specimens, normal penile tissue specimens, normal vaginal tissue specimens, normal esophagus tissue specimens, normal anus tissue specimens, normal adrenal gland tissue specimens, normal ligament tissue specimens, normal intervertebral disk tissue specimens, normal bursa tissue specimens, normal meniscus tissue specimens, normal fascia tissue specimens, normal bone marrow tissue specimens, normal tendon tissue specimens, normal pulley tissue specimens, normal tendon sheath tissue specimens, normal lymph node tissue specimens, or normal nerve tissue specimens. In this embodiment, process 1000 is thus used to generate a database that includes structural, mechanical and cell function indices and optionally the correlation values and cell function map information discussed above for composite tissue types. Such information may then be used as a blueprint for design, engineering and manufacture of composite tissue designs.

Although in the preferred embodiment discussed above, process 1000 is used to generate structural, mechanical and cell function indices for each tissue population of interest. It will be understood by those skilled in the art that all such indices need not be generated for every tissue population of interest, and that the present invention can be used for rational design without the use of all of the indices described herein. For example, for a particular tissue population, only selected ones of the structural indices described herein may be generated and used for the design and manufacture of engineered tissue.

Figure 11:
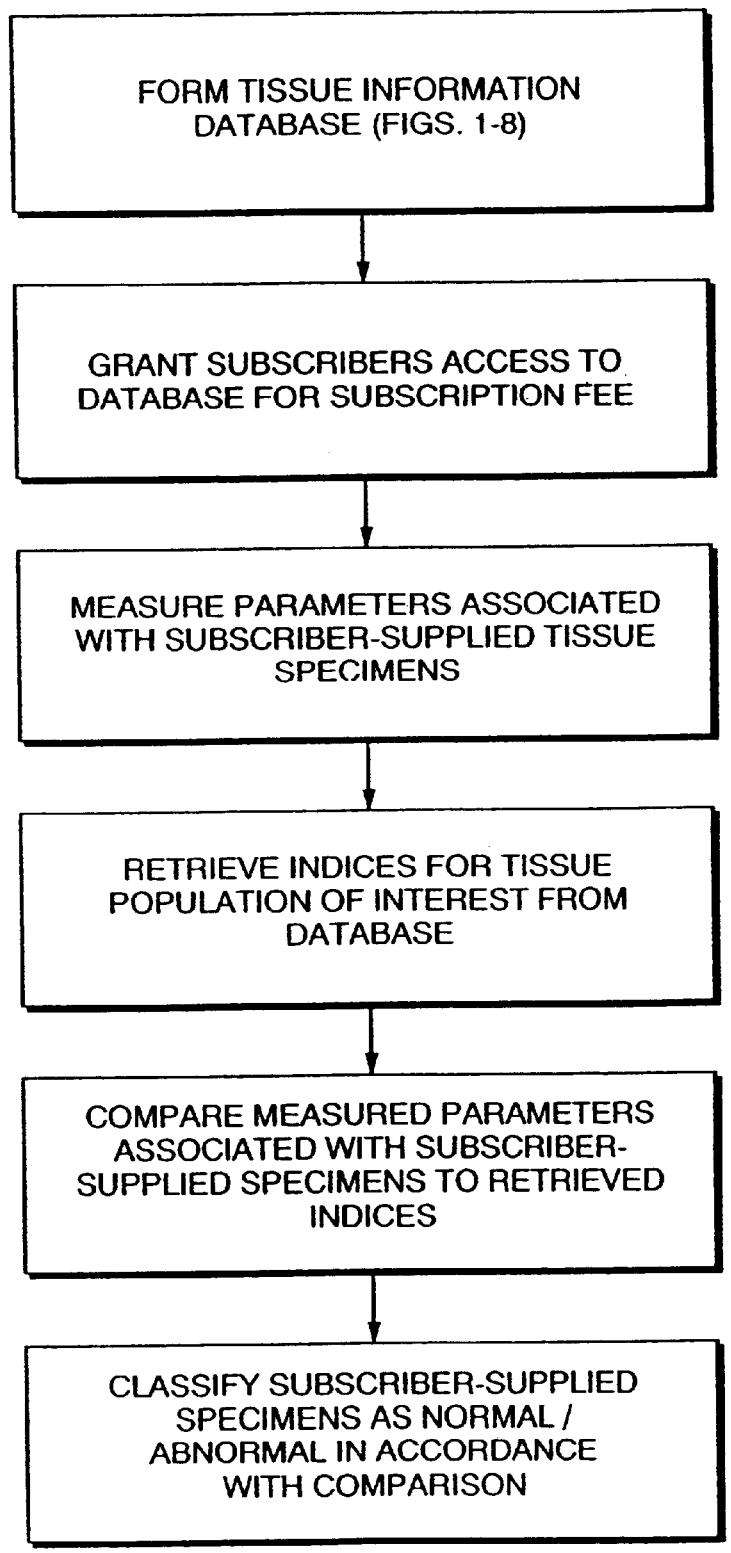
FIG. 11 is a flow diagram showing a method for providing information representative of a plurality of tissue populations to a subscriber and for classifying a user-supplied tissue specimen using such information, in accordance with a preferred embodiment of the present invention.

In accordance with a still further aspect, the tissue database described herein (e.g., FIG. 8) is used to provide information representative of a plurality of tissue types to subscribers over a computer network, such as the internet. Subscribers to such information would include, for example, persons or businesses in the tissue engineering, drug design, gene discovery and genomics research fields. In this embodiment (shown in FIG. 11), each subscriber is granted access to all or part of the database (e.g., a subscriber may granted access to information corresponding to only a particular tissue type or a particular tissue population) based on a subscription fee paid by the user. In addition to using the information in the database for general research purposes, the subscribers may also use such information to classify tissue specimens (e.g., human tissue specimens, animal tissue specimens, plant tissue specimens, food tissue specimens, or manufactured tissue specimens) provided by the subscriber. For example, the user can measure parameters (e.g., structural, mechanical and/or cell function indices) associated with the subscriber's tissue specimens (using the techniques described above) and then compare this information to the corresponding parameters for normal tissue in the database in order to classify the subscriber's tissue specimens as either normal or abnormal. Thus, for example, a subscriber can assess the normalcy of subscriber-supplied tissue specimens which are believed to correspond to normal lung tissue specimens by retrieving the structural, mechanical and/or cell function indices corresponding to normal lung tissue stored in the database, and then comparing these stored indices to corresponding parameters measured from the subscriber-supplied samples. To the extent that the measured parameters deviate from the indices stored in the database for a given subscriber-supplied specimen by more than a threshold amount, the subscriber-supplied specimen will be classified as abnormal. Where the subscriber-supplied tissue specimens correspond to manufactured tissue specimens, measured parameters associated with the subscriber-supplied tissue samples may be compared to the tissue information stored in the database in order to identify normal elements of such manufactured tissue specimens in cases where, for example, such manufactured tissue specimens do not appear normal in total but contain elements that appear and/or function normally.

Although in the embodiment discussed above, the classification of tissue specimens using the tissue information in the database is performed by a subscriber to the database, the classification process can also be performed by the party responsible for creation of the database, in which case the user of the database would likely access the tissue information stored in the database without payment of the subscription fee mentioned above.

The previous description of the preferred embodiments is provided to enable any person skilled in the art to make and use the present invention. The various modifications to these embodiments will be readily apparent to those skilled in the art, and the generic principles defined herein may be applied to other embodiments without the use of the inventive faculty. Thus, the present invention is not intended to be limited to the embodiments shown herein but is to be accorded the widest scope consistent with the principles and novel features disclosed herein.

What is claimed is:

1. A computer implemented method for providing information on tissue specimens to a subscriber comprising the steps of:
   (A) obtaining tissue specimens for a plurality of tissue types from a subset of a population of subjects with shared characteristics,
   (B) imaging each of the tissue specimens,
   (C) determining for each tissue type from the imaging in (B) a distribution of values for each of cell density, matrix density, blood vessel density, and layer thickness,
   (D) calculating average indices for each of the distribution of values in (C),
   (E) calculating dispersion indices for each of the average indices in (D),
   (F) storing the average indices and dispersion indices in a database, and
   (G) providing to the subscriber, in exchange for a fee, access to said average indices and dispersion indices in said database,
      wherein the number of tissue specimens in (A) includes a sufficient number of specimens such that the indices correspond to a statistically significant representation of those indices for the population as a whole.

2. The method of claim 1, wherein the tissue specimens comprise normal tissue.

3. The method of claim 1, wherein the tissue specimens comprise abnormal tissue.

4. The method of claim 1, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

5. The method of claim 1, wherein the tissue types comprise skin.

6. The method of claim 1, wherein the tissue types comprise liver.

7. The method of claim 1, wherein the tissue types comprise kidney.

8. The method of claim 1, wherein the tissue types comprise muscle.

9. The method of claim 1, wherein the tissue types comprise brain.

10. The method of claim 1, wherein the tissue types comprise intestine.

11. A computer implemented method for providing information on tissue specimens to a subscriber comprising the steps of:
    (A) obtaining tissue specimens for a plurality of tissue types from a subset of a population of subjects with shared characteristics,
    (B) assaying each of the tissue specimens,
    (C) determining for each tissue type from the assaying in (B) a distribution of values for each of location, type and amount of DNA,
    (D) calculating average indices for each of the distribution of values in (C),
    (E) calculating dispersion indices for each of the average indices in (D),
    (F) storing the average indices and dispersion indices in a database, and
    (G) providing to the subscriber, in exchange for a fee, access to said average indices and dispersion indices in said database,
       wherein the number of tissue specimens in (A) includes a sufficient number of specimens such that the indices correspond to a statistically significant representation of those indices for the population as a whole.

12. The method of claim 11, wherein the tissue specimens comprise normal tissue.

13. The method of claim 11, wherein the tissue specimens comprise abnormal tissue.

14. The method of claim 11, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

15. The method of claim 11, wherein the tissue types comprise skin.

16. The method of claim 11, wherein the tissue types comprise liver.

17. The method of claim 11, wherein the tissue types comprise kidney.

18. The method of claim 11, wherein the tissue types comprise muscle.

19. The method of claim 11, wherein the tissue types comprise brain.

20. The method of claim 11, wherein the tissue types comprise intestine.

21. The method of claim 11, wherein the tissue types comprise plant tissue.

22. A computer implemented method for providing information on tissue specimens to a subscriber comprising the steps of:
(A) obtaining tissue specimens for a plurality of tissue types from a subset of a population of subjects with shared characteristics,
(B) assaying each of the tissue specimens,
(C) determining for each tissue type from the assaying in (B) a distribution of values for each of location, type and amount of mRNA,
(D) calculating average indices for each of the distribution of values in (C),
(E) calculating dispersion indices for each of the average indices in (D),
(F) storing the average indices and dispersion indices in a database, and
(G) providing to the subscriber, in exchange for a fee, access to said average indices and dispersion indices in said database,
wherein the number of tissue specimens in (A) includes a sufficient number of specimens such that the indices correspond to a statistically significant representation of those indices for the population as a whole.

23. The method of claim 22, wherein the tissue specimens comprise normal tissue.

24. The method of claim 22, wherein the tissue specimens comprise abnormal tissue.

25. The method of claim 22, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

26. The method of claim 22, wherein the tissue types comprise skin.

27. The method of claim 22, wherein the tissue types comprise liver.

28. The method of claim 22, wherein the tissue types comprise kidney.

29. The method of claim 22, wherein the tissue types comprise muscle.

30. The method of claim 22, wherein the tissue types comprise brain.

31. The method of claim 22, wherein the tissue types comprise intestine.

32. The method of claim 22, wherein the tissue types comprise plant tissue.

33. A computer implemented method for providing information on tissue specimens to a subscriber comprising the steps of:
(A) obtaining tissue specimens for a plurality of tissue types from a subset of a population of subjects with shared characteristics,
(B) assaying each of the tissue specimens,
(C) determining for each tissue type from the assaying in (B) a distribution of values for each of location, type and amount of cellular proteins,
(D) calculating average indices for each of the distribution of values in (C),
(E) calculating dispersion indices for each of the average indices in (D),
(F) storing the average indices and dispersion indices in a database, and
(G) providing to the subscriber, in exchange for a fee, access to said average indices and dispersion indices in said database,
wherein the number of tissue specimens in (A) includes a sufficient number of specimens such that the indices correspond to a statistically significant representation of those indices for the population as a whole.

34. The method of claim 33, wherein the tissue specimens comprise normal tissue.

35. The method of claim 33, wherein the tissue specimens comprise abnormal tissue.

36. The method of claim 33, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

37. The method of claim 33, wherein the tissue types comprise skin.

38. The method of claim 33, wherein the tissue types comprise liver.

39. The method of claim 33, wherein the tissue types comprise kidney.

40. The method of claim 33, wherein the tissue types comprise muscle.

41. The method of claim 33, wherein the tissue types comprise brain.

42. The method of claim 33, wherein the tissue types comprise intestine.

43. The method of claim 33, wherein the tissue types comprise plant tissue.

44. A computer implemented method for providing information on tissue specimens to a subscriber comprising the steps of:
(A) obtaining tissue specimens for a plurality of tissue types from a subset of a population of subjects with shared characteristics,
(B) assaying each of the tissue specimens,
(C) determining for each tissue type from the assaying in (B) a distribution of values for each of location, type and amount of cellular lipids, (D) calculating average indices for each of the distribution of values in (C),
(E) calculating dispersion indices for each of the average indices in (D),
(F) storing the average indices and dispersion indices in a database, and
(G) providing to the subscriber, in exchange for a fee, access to said average indices and dispersion indices in said database,
wherein the number of tissue specimens in (A) includes a sufficient number of specimens such that the indices correspond to a statistically significant representation of those indices for the population as a whole.

45. The method of claim 44, wherein the tissue specimens comprise normal tissue.

46. The method of claim 44, wherein the tissue specimens comprise abnormal tissue.

47. The method of claim 44, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

48. The method of claim 44, wherein the tissue types comprise skin.

49. The method of claim 44, wherein the tissue types comprise liver.

50. The method of claim 44, wherein the tissue types comprise kidney.

51. The method of claim 44, wherein the tissue types comprise muscle.

52. The method of claim 44, wherein the tissue types comprise brain.

53. The method of claim 44, wherein the tissue types comprise intestine.

54. The method of claim 44, wherein the tissue types comprise plant tissue.

55. A computer implemented method for providing information on tissue specimens to a subscriber comprising the steps of:
(A) obtaining tissue specimens for a plurality of tissue types from a subset of a population of subjects with shared characteristics,
(B) assaying each of the tissue specimens,
(C) determining for each tissue type from the assaying in (B) a distribution of values for each of location, type and amount of cellular ion distributions,
(D) calculating average indices for each of the distribution of values in (C),
(E) calculating dispersion indices for each of the average indices in (D),
(F) storing the average indices and dispersion indices in a database, and
(G) providing to the subscriber, in exchange for a fee, access to said average indices and dispersion indices in said database,
wherein the number of tissue specimens in (A) includes a sufficient number of specimens such that the indices correspond to a statistically significant representation of those indices for the population as a whole.

56. The method of claim 55, wherein the tissue specimens comprise normal tissue.

57. The method of claim 55, wherein the tissue specimens comprise abnormal tissue.

58. The method of claim 55, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

59. The method of claim 55, wherein the tissue types comprise skin.

60. The method of claim 55, wherein the tissue types comprise liver.

61. The method of claim 55, wherein the tissue types comprise kidney.

62. The method of claim 55, wherein the tissue types comprise muscle.

63. The method of claim 55, wherein the tissue types comprise brain.

64. The method of claim 55, wherein the tissue types comprise intestine.

65. The method of claim 55, wherein the tissue types comprise plant tissue.

66. A computer implemented method for providing information on tissue specimens to a subscriber comprising the steps of:
(A) obtaining tissue specimens for a plurality of tissue types from a subset of a population of subjects with shared characteristics,
(B) analyzing each of the tissue specimens,
(C) determining for each tissue type from the analysis in (B) a distribution of values for modulus of elasticity,
(D) calculating average indices for each of the distribution of values in (C),
(E) calculating dispersion indices for each of the average indices in (D),
(F) storing the average indices and dispersion indices in a database, and
(G) providing to the subscriber, in exchange for a fee, access to said average indices and dispersion indices in said database,
wherein the number of tissue specimens in (A) includes a sufficient number of specimens such that the indices correspond to a statistically significant representation of those indices for the population as a whole.

67. The method of claim 66, wherein the tissue specimens comprise normal tissue.

68. The method of claim 66, wherein the tissue specimens comprise abnormal tissue.

69. The method of claim 66, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

70. The method of claim 66, wherein the tissue types comprise skin.

71. The method of claim 66, wherein the tissue types comprise liver.

72. The method of claim 66, wherein the tissue types comprise kidney.

73. The method of claim 66, wherein the tissue types comprise muscle.

74. The method of claim 66, wherein the tissue types comprise brain.

75. The method of claim 66, wherein the tissue types comprise intestine.

76. The method of claim 66, wherein the tissue types comprise plant tissue.

77. A computer implemented method for providing information on tissue specimens to a subscriber comprising the steps of:

(A) obtaining tissue specimens for a plurality of tissue types from a subset of a population of subjects with shared characteristics, (B) analyzing each of the tissue specimens, (C) determining for each tissue type from the analysis in (B) a distribution of values for mechanical strength, (D) calculating average indices for each of the distribution of values in (C), (E) calculating dispersion indices for each of the average indices in (D), (F) storing the average indices and dispersion indices in a database, and (G) providing to the subscriber, in exchange for a fee, access to said average indices and dispersion indices in said database, wherein the number of tissue specimens in (A) includes a sufficient number of specimens such that the indices correspond to a statistically significant representation of those indices for the population as a whole.

78. The method of claim 77, wherein the tissue specimens comprise normal tissue.

79. The method of claim 77, wherein the tissue specimens comprise abnormal tissue.

80. The method of claim 77, wherein the tissue specimens comprise normal and abnormal tissue of the same tissue type, and wherein in the determination of distribution of values and corresponding indices, data from normal tissue is used to determine a distribution of values and corresponding indices for normal tissue and data from abnormal tissue is used to determine a distribution of values and corresponding indices for abnormal tissue.

81. The method of claim 77, wherein the tissue types comprise skin.

82. The method of claim 77, wherein the tissue types comprise liver.

83. The method of claim 77, wherein the tissue types comprise kidney.

84. The method of claim 77, wherein the tissue types comprise muscle.

85. The method of claim 77, wherein the tissue types comprise brain.

86. The method of claim 77, wherein the tissue types comprise intestine.

87. The method of claim 77, wherein the tissue types comprise plant tissue.

* * * * *